(12) United States Patent
Sharma et al.

(10) Patent No.: US 10,724,040 B2
(45) Date of Patent: Jul. 28, 2020

(54) MRNA SEQUENCES TO CONTROL CO-TRANSLATIONAL FOLDING OF PROTEINS

(71) Applicant: The Penn State Research Foundation, University Park, PA (US)

(72) Inventors: Ajeet K. Sharma, State College, PA (US); Edward P. O'Brien, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 290 days.

(21) Appl. No.: 15/212,164

(22) Filed: Jul. 15, 2016

(65) Prior Publication Data

US 2017/0016008 A1 Jan. 19, 2017

Related U.S. Application Data

(60) Provisional application No. 62/192,913, filed on Jul. 15, 2015.

(51) Int. Cl.
| | |
|---|---|
| *C12N 15/67* | (2006.01) |
| *G16B 15/20* | (2019.01) |
| *G16B 30/00* | (2019.01) |
| *G16B 25/10* | (2019.01) |

(52) U.S. Cl.
CPC ............ *C12N 15/67* (2013.01); *G16B 15/20* (2019.02); *G16B 25/10* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 7,888,489 | B2 | 2/2011 | Roubos et al. |
| 7,901,905 | B2 | 3/2011 | Frazer |
| 8,326,547 | B2 | 12/2012 | Liu et al. |
| 8,812,247 | B2 | 8/2014 | Roubos et al. |
| 2002/0157135 | A1 | 10/2002 | Frazer et al. |
| 2008/0046192 | A1 | 2/2008 | Lathrop et al. |
| 2008/0076161 | A1 | 3/2008 | Angov et al. |
| 2012/0040367 | A1 | 2/2012 | Frazer |
| 2013/0074218 | A1 | 3/2013 | Frazer |
| 2013/0149699 | A1 | 6/2013 | Barral et al. |
| 2013/0183664 | A1 | 7/2013 | Welch et al. |
| 2013/0266989 | A1 | 10/2013 | Parks et al. |
| 2014/0244228 | A1 | 8/2014 | Lee et al. |
| 2014/0273091 | A1 | 9/2014 | Acton et al. |
| 2015/0152408 | A1 | 6/2015 | Basu et al. |

FOREIGN PATENT DOCUMENTS

| | | |
|---|---|---|
| EP | 1002091 B1 | 2/2012 |
| WO | 8900604 A1 | 1/1989 |
| WO | 0044926 A1 | 8/2000 |
| WO | 03070957 A2 | 8/2003 |
| WO | 2008144012 A2 | 11/2008 |
| WO | 2009009743 A2 | 1/2009 |
| WO | 2014014950 A1 | 1/2014 |
| WO | 2015048989 A1 | 4/2015 |

OTHER PUBLICATIONS

Angov et al. Heterologous Protein Expression Is Enhanced by Harmonizing the Codon Usage Frequencies of the Target Gene with those of the Expression Host PLoS one vol. 3 article e2189 (Year: 2008).*
Bradel-Tretheway et al. Effects of codon-optimization on protein expression by the human herpesvirus 6 and 7 U51 open reading frame Journal of Virological Methods vol. 111, pp. 145-156 (Year: 2003).*
Chung, et al, "Computational Codon Optimization of Synthetic Gene for Protein Expression", BMC Systems Biology, 2012, 6:134.
Obrien, et al. "Kinetic Modelling Indicates that Fast-Translating Codons Can Coordiante Cotranslational Protein Folding by Avoiding Misfolded Intermediates", Nature Communications, 2014, 11 pages.
Hatfield, et al. "Optimizing Scaleup Yield for Protein Production: Computationally Optimized DNA Assembly (CODA) and Translation Engineering", National Institutes of Health (2007) 13: pp. 27-42.
Angov, et al. "Heterologous Protein Expression Is Enhanced by Harmonizing the Codon Usage Frequencies of the Target Gene with Those of the Expression Host", PloS One (2008) vol. 2, Issue 5.
Obrien, et al. "Understanding the Influence of Codon Translation Rates on Cotranslational Protein Folding" National Institutes of Health (2014) pp. 1536-1544.

* cited by examiner

*Primary Examiner* — John S Brusca
(74) *Attorney, Agent, or Firm* — McKee, Voorhees & Sease, PLC

(57) ABSTRACT

This invention relates to optimized heterologous production of properly folded and functional proteins. The present invention provides systems and methods involving determination of the optimal mRNA sequence, based on the underlying rates at which codons are translated and folding kinetic of nascent-protein, that maximizes co-translational protein folding of domains in order to maximize the proper folding and quality of the protein produced. The codon translation rates can be determined in a number of ways, including theoretical estimation and, preferably, through experimental data, such as ribosome profiling. The determination of an optimal mRNA sequence through the utilization of codon translation rates under a particular set of conditions allows for application of the method irrespective of the organism from which the protein in question was originally derived.

8 Claims, 12 Drawing Sheets

MRNA SEQUENCES TO CONTROL CO-TRANSLATIONAL FOLDING OF PROTEINS

TECHNICAL FIELD

This invention relates to optimized heterologous production of properly folded and functional proteins. In particular, the present invention includes systems and methods involving determination of the optimal mRNA sequence, based on the underlying rates at which codons are translated and folding kinetics of nascent-protein, which maximizes co-translational protein folding of domains in order to maximize the proper folding and quality of the protein produced. The translation rates and folding kinetics can be determined in a number of ways, including theoretical estimation or through the use of an empirical formulae and, preferably, through experimental data. Experimental data may include, for example, ribosome profiling to determine translation rates and fluorescence resonance energy transfer (FRET) analysis to determine folding kinetics of nascent-protein requires. The determination of an optimal mRNA sequence through the utilization of translation rates under a particular set of conditions allows for application of the method irrespective of the organism from which the protein in question was originally derived.

BACKGROUND OF THE INVENTION

Precise timing is often required for the accuracy and efficiency of the numerous co-translational processes acting on a nascent protein, which help it to attain its functionality. Therefore, the ability of a nascent protein molecule to form its native structure and acquire its biological function can be influenced by the rate at which individual codon positions in an mRNA molecule are translated by the ribosome. Synthesize a signal sequence too fast and signal recognition particle (SRP) may not be able to bind to it, resulting in a decreased probability of successful co-translational translocation of the nascent protein through the SEC-translocon. Change the translation rate at critical codon positions and a protein will switch from co-translational folding to misfolding, resulting in an increased population of insoluble or soluble, but nonfunctional, protein. For these reasons, evolutionary selection pressures have shaped codon usage bias in organisms in part to maximize the efficiency of these co-translational processes by tuning the translation-rate profile along the coding sequence through synonymous codon mutations as shown in FIG. 1(a).

The physical rules governing why changes in translation rate at some codon positions will have a significant effect on nascent protein folding though changes at other positions will have little to no effect are unknown. Previous work using synonymous mRNA sequence variants of the human anti-IgE antibody found that they produced protein of varying solubility and functionality. Some synonymous mutations had no effect on these properties while others decreased or increased the protein's specific activity by as much as tenfold. These results support the idea that synonymous mutations at different locations can alter the likelihood of co-translational folding to varying degrees.

Other previous work has attempted to utilize synonymous codon to modulate protein expression in heterologous systems. In general, these work used optimization methods intended to maximize the quantity of protein produced, which in some cases also helped to produce properly folded proteins. These approaches mostly relied on adopting the codon usage of the organism in which the protein in question is endogenously expressed with the codon usage for the heterologous expression cell. In addition, these methods were not developed to optimize the folding, function, and/or quality of the protein expressed in heterologous systems in a user-prescribed manner.

One prior approach is codon harmonization (Angov, E., Hillier, C. J., Kincaid, R. L. & Lyon, J. A. Heterologous protein expression is enhanced by harmonizing the codon usage frequencies of the target gene with those of the expression host. PLoS ONE 3, e2189 (2008)), which relies on replicating the codon usage in the organism in which the protein is endogenously produced (e.g. the human codon usage for a human protein) in the expression organism (e.g. *E. coli*). This approach is aimed at enhancing the fraction of functional or soluble proteins in a given heterologous host system. The translation rate of a codon is dictated in part by the concentrations of corresponding iso-acceptor tRNA molecules, which is found to be correlated with the frequency of codon usage in unicellular organisms. The approach picks codon sequences for the heterologous system that reproduces the translation rates in the endogenous organism. Thus, for example, to express a human protein in *E. coli*, codon usage frequencies of its mRNA sequence should be harmonized with the human cells. This approach relies entirely on the codon usage frequencies of native and heterologous host species.

A similar previously used approach is modulating translation speed by considering tRNA pool size as a sole determinant of the codon translation rates (U.S. Patent Pub. No. US20130149699A1). Using the kinetic effects of the wobble base pairing, this approach seeks to replicate the translation rate profile of the endogenous protein expression in the heterologous system.

The previously adopted approaches prioritized quantity of heterologous protein production. However, success of these approaches are subjected to the validity of underlying assumptions used by these approaches. Therefore, there is a need for methods and systems that optimize the folding, quality, and function of heterologously expressed proteins under all circumstances.

Furthermore, such approaches do not explicitly account for the profound effect that translation-elongation rates can have on nascent protein behavior, or the combined effect of translation-initiation and translation-elongation.

The present invention focuses on the process of co-translational folding, and utilizes synonymous codon translation rates and the rates of interconversion between states of the nascent protein determined for the protein production conditions to rapidly design mRNA sequences that quantitatively control nascent protein folding at each step during protein biogenesis. The present invention also provides the ability to test the predictions from this framework against coarse grained molecular dynamics simulations of co-translational folding.

Other objects, advantages and features of the present invention will become apparent from the following specification taken in conjunction with the accompanying drawings. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

SUMMARY

The present invention encompasses methods and systems that allow for optimized heterologous production of properly folded and functional proteins. In particular, the systems and methods include the determination of the actual translation rates, including synonymous codon translation rates and initiation rates, and use them to optimize the mRNA sequence that produces desired co-translational protein folding in order to maximize the proper folding, structure, and quality of the protein produced. The translation rates can be determined in a number of ways, including theoretical estimation and, preferably, through experimental analysis, such as ribosome profiling. The determination and application of the actual translation rates for a particular set of conditions allows for adaptation of the system to produce optimally folded and function protein under those conditions, irrespective of the organism from which the protein in question was originally derived. In addition, the rates for folding kinetics of the nascent protein can be estimated by using theoretical approaches and FRET experiments.

In one aspect, the invention includes methods of enhancing the quality of heterologous protein production in a cell or population of cells. The cell or population of cells can be in a cell culture or a bioreactor. The methods can comprise determining the desired conformation of a protein produced by a cell; determining of rates of interconversion between different states of said protein; determining the actual codon translation rates for an mRNA molecule encoding said protein having said desired conformation; generating an optimized mRNA sequence incorporating an optimized codon sequence based on the rates of said protein's interconversion between different states and the translation rates in host organism; producing an oligonucleotide having or encoding said optimized mRNA sequence; and providing said cell with said oligonucleotide. In a further aspect, determining the actual translation rate for an mRNA molecule encoding said protein having said desired conformation comprises theoretical estimation or experimental analysis. In a further aspect, the experimental analysis comprises ribosome profiling.

In another aspect, the invention includes enhanced heterologous protein production systems. The systems can comprise a cell or population of cells and an oligonucleotide having or encoding an optimized mRNA sequence, wherein said optimized mRNA sequence incorporates a coding sequence based on the desired states of said protein, the rates of interconversion between different states of the protein, and the actual translation rates necessary for desired co-translational folding of the protein. The population of cells can comprise a cell culture or a bioreactor.

Compared to other strategies for influencing nascent protein behavior, the present invention provides a number of demonstrable benefits. Conventional techniques, referred to as codon optimization methods, frequently focus on designing mRNA sequences that maximize the amount of protein that can be produced by an mRNA molecule. They often utilize various characteristics of codons as surrogates for codon translation rates, such as whether they are rare or common in the organism's genome, or have low or high cognate tRNA abundances. For example, a technique in heterologous protein expression is to use the most common synonymous codon at each position in an mRNAs coding sequence based on the assumption that common codons are translated quickly and more accurately. What sets the present invention apart from these other methods is that the present invention explicitly accounts for the influence of translation dynamics and co-translational protein behavior. Thus, the present invention can be used to design proteins that avoid misfolding and thereby increase the amount of functional protein in heterologous expression.

BRIEF DESCRIPTION OF THE FIGURES

FIG. 13(a-d) shows Monte Carlo-master-equation-based framework successfully optimizes mRNA sequences that reproduce user-defined co-translational profiles for E. coli proteins (a-d). Folding probabilities of the (a) first domain of SYK1, (b) third domain of TRXB, (c) fourth domain of FDHF, and (d) second domain of AAT proteins are plotted as a function of nascent chain length during synthesis. Different co-translational profiles of the same protein are plotted in a different color and labeled by an integer index 1, 2, or 3. User-defined target co-translational profiles are plotted with dashed lines, whereas optimized co-translational profiles are plotted with discrete data points. In (d), the dashed blue line is the equilibrium folding curve of AAT protein.

Figure 1A:
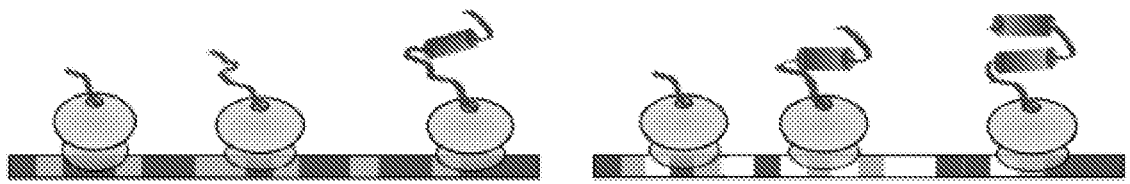
FIG. 1(a) is an illustration of changes in co-translational folding due to changes in the translation profiled induced by synonymous codon substitutions. The different shading of the bars indicates the fast, medium, and slow translating codons in the mRNA sequences that encored for the same protein.

Various embodiments of the present invention are described in detail with reference to the drawings. The reference to various embodiments does not limit the scope of the invention. Figures represented herein are not limitations to the various embodiments according to the invention and are presented for exemplary illustration of the invention.

DETAILED DESCRIPTION OF THE INVENTION

It is to be understood that all terminology used herein is for the purpose of describing particular embodiments only, and is not intended to be limiting in any manner or scope. All units, prefixes, and symbols may be denoted in SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein the singular forms "a," "an" and "the" can include plural referents unless the content clearly indicates otherwise.

As used herein, the term "co-translational" refers to any process involving the maturation or delivery of a protein that occurs during the process of translation. The term "co-translational folding" refers to the process by which the amino acid sequence of a polypeptide folds to assume its unique tertiary structure during protein synthesis. The term "co-translational profile" refers to the steady-state probability of a protein domain being in a particular state as a function of the nascent chain length during synthesis.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as E. coli, or eukaryotic cells such as yeast, plant, insect, amphibian, or mammalian cells.

As used herein, "nucleic acid" includes reference to a deoxyribonucleotide or ribonucleotide polymer in either single- or double-stranded form, and unless otherwise limited, encompasses conservatively modified variants and known analogues having the essential nature of natural nucleotides in that they hybridize to single-stranded nucleic acids in a manner similar to naturally occurring nucleotides (e. g., peptide nucleic acids).

As used herein "synonymous codon" refers to a series of three nucleotides (a triplet) that encodes the same specific amino acid residue in a polypeptide chain or for the termination of translation (stop codons) as another triplet. There are 64 different codons (61 codons encoding for amino acids plus 3 stop codons) but only 20 different translated amino acids. The overabundance in the number of codons allows many amino acids to be encoded by more than one codon. Because of such redundancy it is said that the genetic code is degenerate. Different organisms often show particular preferences for one of the several codons that encode the same amino acid—that is, a greater frequency of one will be found than expected by chance. Synonymous codon substitutions change the translation rate at specific positions within an mRNA's coding sequence without changing the encoded protein's amino acid sequence and can alter a nascent protein's ability to co-translationally fold and function. The present invention provides a system and methods for controlling of nascent protein chain folding during translation by providing optimized mRNA sequences using synonymous codons.

As used herein, the term "translation rate" can refer to elongation rate (i.e. codon translation rate) and initiation rates (i.e. the rate at which translation initiates).

Methods for Producing Optimized mRNA Sequences for Protein Production

In one aspect, the present invention provides methods for optimizing mRNA sequences for protein production. The method provides a better way of producing mRNA sequences for production of proteins in heterologous systems, such as for example cell culture or bioreactor. In one aspect, the method utilizes an algorithm that accounts for a variety of microscopic rates related to translation. The variables that are accounted for by the algorithm include rates of translation, the states or conformations that the protein in question can populate, and rates of interconversion among various states or conformations. By accounting for these microscopic rates, the algorithm provides control over co-translational behavior in protein production. This allows protein production to be optimized for maximized or enhanced production of protein in the desired conformation or state by the heterologous production system.

In one aspect, the methods utilize translation rates that are provided in relation to the heterologous expression system. The translation rates can be obtained from a database or other existing source, or can be experimentally determined. The translation rates can vary among different systems; for example, the translation rates can be different as between protein production in yeast and protein production in insect cells, and can even be different as between different yeast species or the same yeast species under different culture conditions. In another aspect, using synonymous mutations the present invention can modify the elongation rate, the initiation rate, or both. Translation rates can be the rates for the elongation phase of protein translation (i.e. the codon translation rate) or the initiation phase of protein translation (i.e. the rate at which translation is initiated). These rates can be different for the same expression system under the same conditions. In some embodiments, both the elongation phase and the initiation phase translation rates can be used.

The protein to be produced may have more than one state or conformation. According to the present invention, the methods include selecting a particular conformation in which the protein is to be produced. The conformations or states can include unfolded, folded, intermediate, and misfolded states. The protein can have one or more intermediate states, and one or more misfolded states. The one or more intermediate states can be varying degrees of protein folding, which can be associated with how much of the protein has been translated. The method can be optimized for or account for a desired state or conformation of the protein of interest.

In another aspect, the rates of conversion between or among various states or conformations of the protein of interest can be provided. The interconversion rates can be between one or more of the states or conformations of the protein of interest. For example, rates can be for interconversion of the domain from its unfolded to folded state, and from the folded to the unfolded state. The interconversion rates can be obtained from a database, theoretical models, FRET experiments or other sources. Alternatively, the interconversion rates can be calculated or experimentally determined, including by theoretical models.

In a further aspect, the methods utilize an algorithm to produce the optimized mRNA sequence for the protein to be produced. The algorithm accounts for underlying microscopic rates to control the co-translational behavior. In one further aspect, the algorithm searches the entirety of the synonymous codons that could encode the amino acid sequence of the protein, and selects the best set of codons (i.e. mRNA sequence) to account for the expression conditions, rates of translation, conformational states, and rates of interconversion in order to optimize the production of the protein in the desired conformational state.

Implementation of the optimization framework requires the accurate prediction of the effect that a change in a codon position's translation rate will have on a protein's co-translational profile. Therefore, an analytical expression for the steady-state probability that a protein will be in any one of N possible states at each nascent chain length during its synthesis can be derived. The probability that a nascent chain of length j is in state l at time t is denoted by $P_l(j,t)$, where $l=\{1, 2, \ldots, N\}$. The master equation governing the time evolution of $P_l(j,t)$ can be written as $$\frac{dP_l(j,t)}{dt} = \sum_{i=1, i \neq l}^{N} P_i(j,t) k_{il}(j) - \sum_{i=1, i \neq l}^{N} P_l(j,t) k_{li}(j) + P_l(j-1,t) \omega_l(j) - P_l(j,t) \omega_l(j+1) \quad \text{(Equation 1)}$$

where $k_{il}(j)$ is the rate at which state i interconverts with state l at codon position j and $\omega_l(j)$ is the rate at which codon j−1 is translated when the nascent chain is in state l. The first and second terms of the right-hand side of equation 1 determine the gain and loss in $P_l(j,t)$ arising from the folding kinetics of the protein domain; the third and fourth terms are the gain and loss contributions from translation-elongation kinetics. Equation 1 can also be written as a matrix equation $$\frac{dP(j,t)}{dt} = M(j)P(j,t) - T(j)P(j-1,t) \quad \text{(Equation 5)}$$

where $P(j,t)$ is a column vector of the state probabilities $$P(j,t) = \begin{bmatrix} P_1(j,t) \\ P_2(j,t) \\ \vdots \\ P_N(j,t) \end{bmatrix} \quad \text{(Equation 6)}$$

and $$Mj = \begin{bmatrix} -\left(\omega_1(j+1) + \sum_{l=2}^{N} k_{1l}\right) & k_{12}(j) & \cdots & k_{N1}(j) \\ k_{12}(j) & -\left(\omega_2(j+1) + \sum_{l=1, l\neq 2}^{N} k_{2l}\right) & \cdots & k_{N2}(j) \\ \vdots & \cdots & \ddots & \vdots \\ k_{N1}(j) & \cdots & \cdots & -\left(\omega_N(j+1) + \sum_{l=1}^{N-1} k_{2l}\right) \end{bmatrix}$$ (Equation 7)

and $$T(j) = \begin{bmatrix} -\omega_1(j) & 0 & \cdots & 0 \\ 0 & -\omega_2(j) & \cdots & 0 \\ \vdots & \vdots & \ddots & \vdots \\ 0 & 0 & \cdots & -\omega_N(j) \end{bmatrix}$$ (Equation 8)

M(j) and T(j) are N×N-size transition matrices describing the transitions between state in the nascent protein. In the expressions for M(j) and T(j), $\omega_k(j+1)$ is the rate at which $j^{th}$ codon is translated when the nascent chain is in state k and $k_{il}(j)$ is the rate of transitioning from state i to state l at codon position j. Solving the master equation at steady state conditions results in the recursive relation $$P(j)=M(j)^{-1}T(j)P(j-1)$$ (Equation 9)

That is, the steady-state probabilities (P(j)) at codon j depend on what happened at all earlier codon positions (P(j−1)). The elements of P(j) are denoted as $P_1(j)$, $P_2(j)$, . . . ,$P_{N-1}(j)$ and $P_N(j)$. Translation, in this model, involves an open system; therefore, the sum of the probabilities of populating different states at codon position j is not equal to one. For this reason, we then normalized these probabilities at each codon position by dividing the term $\Sigma_{i=1}^{N}P_i(j)$.

In a further aspect, the methods can also comprise providing to a cell a polynucleotide that has or encodes the optimized mRNA sequence. The mRNA sequence is understood to be non-naturally occurring as a result of the described method. The mRNA sequence could, for example, be provided directly to a cell, or in a more particular embodiment, a DNA polynucleotide can be provided to the cell, the transcription of which will yield the optimized mRNA sequence. The provision of polynucleotides can be performed by any technique known in the art, including but not limited to transformation, calcium phosphate transfection, DEAE-dextran transfection, electroporation, and liposome-mediated transfection. The cells may be transiently or stably transformed, and may be transformed with more than one polynucleotide construct. The invention also includes polynucleotides comprising or encoding the optimized mRNA sequences. The invention further includes cells comprising such polynucleotides comprising or encoding the optimized mRNA sequences. The invention further comprises the protein produced by such cells.

The methods and systems of the present invention can be adapted for use of a variety of heterologous expression cells. The heterologous expression cells can be prokaryotic or eukaryotic, including, for example, bacteria, cyanobacteria, algae, yeast, protozoa, plant cells, insect cells, and animal cells.

In another aspect, the systems of the present invention can include heterologous expression by cells, for example, in cell culture or bioreactors. The optimization of oligonucleotide sequences to enhance the folding and function of a heterologously expressed protein may be modified to account for the particular culture or growth conditions.

In a further embodiment, the method can comprise performing the steps a first time and a second time, wherein the first performance of the method steps utilizes translation rates that are one of either translation-elongation rates (i.e., codon translation rates) or translation-initiation rates, and the second performance of the method steps utilizes translation rates that are one of either translation-elongation rates or translation-initiation rates, and wherein the translation rates for the second performance of the method steps are not the same as the translation rates for the first performance of the method steps. For example, the first performance of the method steps may utilize translation-initiation rate, and the second performance of the method steps may utilize translation-elongation rates. Alternatively, the first performance of the method steps may utilize translation-elongation rates, and the second performance of the method steps utilizes translation-initiation rates. In yet another exemplary embodiment, the first performance of the method steps utilizes translation-elongation rates, and the second performance of the method steps utilizes translation-elongation rates, but the rates are different, for example because the first elongation translation rates are obtained from a database, and the second elongation translation rates are obtained by theoretical modeling.

Figure 2A:
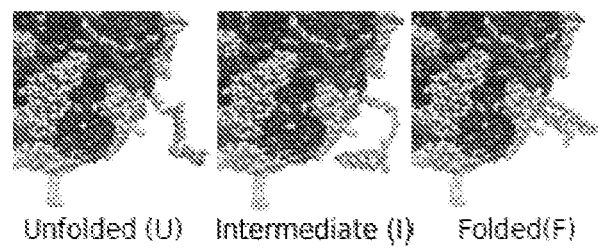
FIG. 2(a) illustrates structures from coarse-grained simulation of the ribosome nascent chain complexes which are shown with the MIT protein in the unfolding, intermediate, and folded states.
Figure 2B:
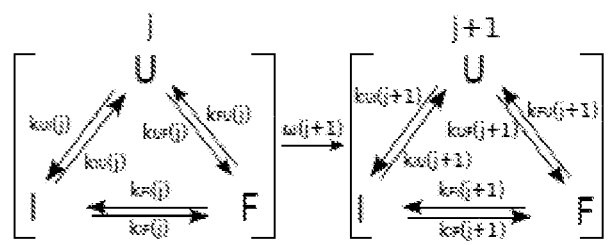
FIG. 2(b) shows a parallel co-translational folding reaction scheme.

The co-translational folding process of a protein domain can be characterized by its co-translational profile, which is the steady-state probability of the domain being in a particular state as a function of the nascent chain length during synthesis. The states that a domain in a multi-domain protein can populate during its synthesis include unfolded (U), intermediate (I), folded (F) and misfolded (M) states. Such domain-wise folding can occur before the full-length protein has been synthesized (FIG. 2(a)). Under physiological conditions, the folded state is often the most stable state that a protein can populate. Misfolded states are meta-stable, and contain non-native structure. Intermediates are partly folded and form transiently-stable states which can transition to either the folded or misfolded states as shown in (FIG. 2(b)).

Controlling co-translational folding using synonymous mutations means being able to alter this co-translational profile to match a user-defined co-translational profile through the appropriate choice of synonymous codons. These synonymous codons may alter the translation-rate profile along the coding sequence. As a consequence, controlling co-translational folding requires rational alteration of an mRNA's translation-rate profile. Therefore, any framework to control co-translational folding must be able to predict how changing the translation rate changes a protein's co-translational profile, and also it must be able to efficiently search the astronomically large synonymous-codon space of a transcript's coding sequence to find the optimal mRNA sequence that is predicted to reproduce the user-defined co-translational profile.

Figure 1B:
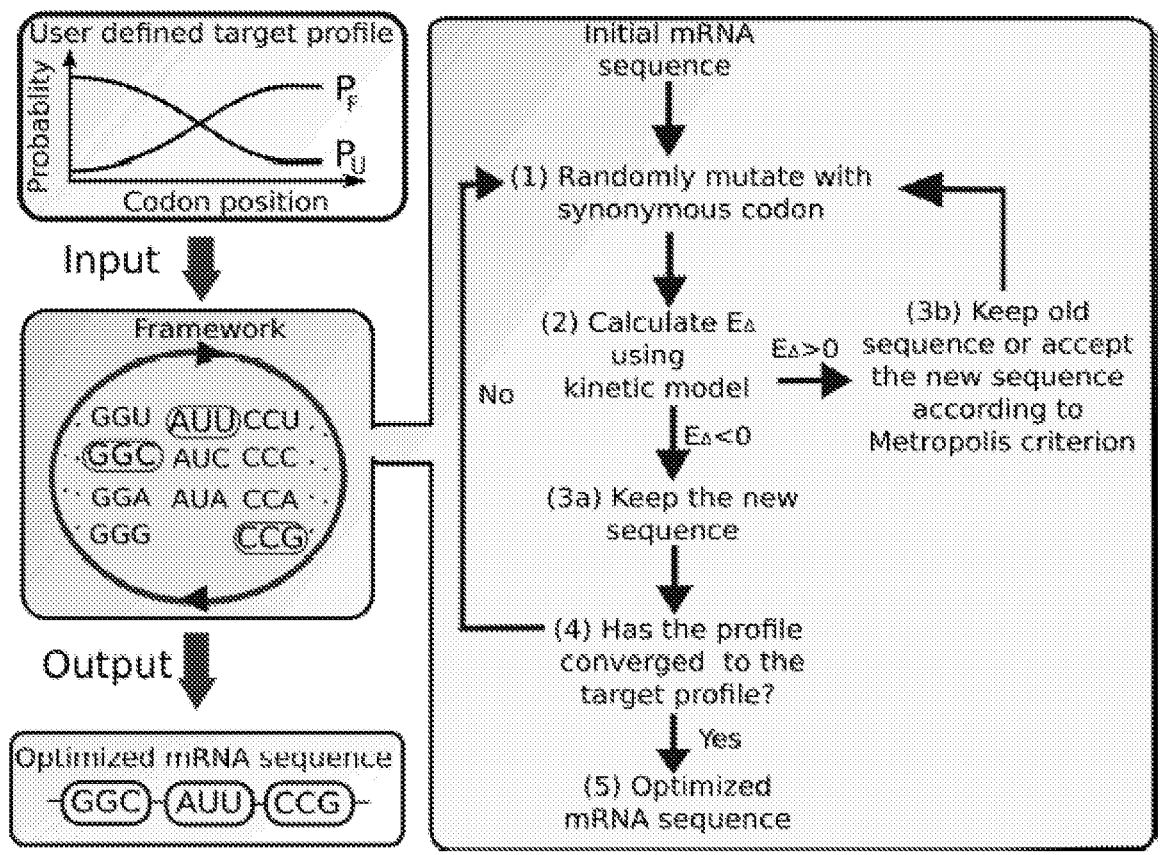
FIG. 1(b) is a flow chart illustrating the operation of an exemplary embodiment of the present invention.

Recent studies have found that a Markov-state analysis is one way to accurately predict the impact that changing codon translation rates has on a protein's co-translational profile, provided the interconversion rates between states are known. And the Metropolis Monte Carlo algorithm is a standard technique in the physical sciences to search large state spaces for optimal solutions. Accordingly, in one aspect of the invention, the Monte-Carlo-Master-equation based framework shown in FIG. 1(b) may be used to rationally design mRNA sequences to control co-translational folding. According to a further aspect of the invention, a user-defined co-translational profile is supplied as an input. Then an initial starting mRNA sequence is randomly mutated with a single synonymous codon substitution to create a new sequence (step 1, FIG. 1(b)). The co-translational profiles of the old and new sequences are predicted using a master equation, and the deviations of these profiles from the user-defined co-translational profile are calculated. These deviations are then used to compute $E_A$ (Equation 3), which is employed in the Metropolis criterion to either accept or reject the newly mutated mRNA sequence. This process is iterated until an mRNA sequence is found that results in the best agreement with the target co-translational profile. According to a further aspect of the invention, the master equation approach, used in step 2 (FIG. 1(b)), is accurate enough to predict the impact of changing codon translation rates at specific codon positions.

According to a further aspect of the invention, the systems and methods are used to design mRNA sequences that finely control nascent protein folding behavior by exploiting the non-equilibrium (i.e., kinetically-controlled) nature of the co-translational folding process. First, the desired co-translational behavior is defined as the probability of a protein being in a particular state at different nascent chain lengths during synthesis, which is referred to as the co-translational profile. Once the co-translational profile is supplied as input, the astronomically-large mRNA sequence space that encodes the protein comprising the various combinations of synonymous codons is searched to find the optimal mRNA sequence that most closely reproduces the user-defined co-translational profile. Varying the mRNA sequence through synonymous codon mutations alters the rate at which the ribosome slides along it. Provided the rate matrix M(j) and codon translation rates are known, and regardless of their molecular origin, our method is applicable to all the kingdoms of life. Thus, the method determined the optimal translation-rate profile that guides a protein's co-translational folding in a user-defined manner. In this way, translation-elongation dynamics are used in our framework to control co-translational folding.

In a further aspect of the invention, the different states a nascent protein populates during translation are determined, and the interconversion rates between those states and individual translation rates are determined. In a further aspect, high-throughput and single molecule experiments can be used to measure some or all of these quantities. For example, ribosome profiling data can be used to estimate in vivo codon translation rates. A number of techniques can provide a measure of co-translational folding curves, for example, FactSeq can evaluate equilibrium co-translational profiles. Advances in these techniques in the near future may provide measurements of co-translational profiles occurring during continuous translation. Fluorescence based techniques can be used to probe interconversion rates of co-translationally folding domains. Even when such data are not available, there are theoretical models that predict an organism's translation rates and a domain's bulk folding and unfolding rates. Thus, the methods and systems of the present invention can be utilized for various proteins using measured and estimated rates currently available in the literature.

In a further aspect, unlike other approaches, the methods and systems of the present invention can predict their own success or failure. For example, for the user-defined profile in FIG. 4(f), our framework predicted that the best an mRNA sequence could do is reproduce the profile between codon positions 80 and 105, and fail elsewhere, which is what was observed when the explicit coarse-grained simulations of protein synthesis were run.

The present invention can be extended to design mRNA sequences to control other co-translational nascent protein behaviors. In eukaryotes and prokaryotes, there are at least eleven different co-translational processes that can act on a nascent chain during its synthesisa. Each one of these processes can be represented as a different state in the co-translational reaction network (FIG. 2b), resulting in a modification to the rate matrix M(j) used in the master equation (Eq. 5). Besides this, no changes are required to our framework (FIG. 1(b)) to account for these additional processes. Extending the model in this way would open up a large range of possibilities, such as making it possible to design mRNA sequences that minimize the chances of premature nascent protein degradation and maximize the co-translational efficiency of secretary proteins into the endoplasmic reticulum.

System

In another embodiment, the present invention involves a system for producing an optimizing mRNA sequence for heterologous production of a protein. In one aspect the system comprises a computing environment or device for executing a method of determining an optimized mRNA sequence for producing a properly folded protein for heterologous production in a cell. The computing environment or device executes a method for determining an optimized mRNA sequence, as described herein, through the implementation of an algorithm that selects the best set of codons to produce an mRNA sequence that encodes the protein of interest. In a further aspect, the algorithm carries out the selecting in a manner that accounts for the expression conditions, rates of translation, conformational states, and rates of interconversion for production of said protein in the selected conformational state.

In another aspect, the invention includes a computing device for executing a method of producing an optimized mRNA sequence for producing a protein having a desired conformation. The method may comprise the steps of obtaining the amino acid sequence for a protein, obtaining conditions for expression of said protein, obtaining rates of translation for said conditions of expression, obtaining the conformational states said protein can populate, obtaining the rates of interconversion among the conformational states, obtaining a desired conformational state for production of said protein, and producing an optimized mRNA sequence for said protein in the selected desired conformational state using an algorithm that accounts for the obtained rates of translation, conformational states, and rates of interconversion.

In another aspect, the invention includes one or more computer-storage media having computer-executable instructions embodied thereon that, when executed, perform a method of providing an optimized mRNA sequence for production of a heterologous protein in a cell, the method comprising searching a source of synonymous codons for the amino acid sequence of said protein, and selecting the best set of codons to produce an mRNA sequence, wherein said selecting accounts for the expression conditions, rates of translation, conformational states, and rates of interconversion for production of said protein in the selected conformational state. In a further aspect, the selecting utilizes an algorithm that accounts for underlying microscopic rates to control co-translational behavior and searches the entirety of the synonymous codons that could encode the amino acid sequence of the protein, and selects the best set of codons to account for the expression conditions, rates of translation, conformational states, and rates of interconversion in order to optimize the production of the protein in the desired conformational state, as described elsewhere in this disclosure.

In one aspect, the system comprises a computing environment. The computing environment may comprise a general purpose computing device in the form of a control server. Exemplary components of the control server may comprise a processing unit, internal system memory, and a suitable system bus for coupling various system components, including one or more databases, with the control server. The system bus may be any of several types of bus structures, including a memory bus or memory controller, a peripheral bus, and a local bus, using any of a variety of bus architectures. Exemplary architectures may comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The computing device typically includes therein, or has access to, a variety of computer-readable and computer-storage media, such as a database. The control server may be coupled to one or more databases or third party computing devices that comprise data comprising amino acid sequences of proteins, synonymous codons. Computer-storage media may be any available media that is accessible by the control server, a third-party computing device, a peripheral device, and/or the computing device and may be removable and/or non-removable media. Computer-storage media may be implemented in any method or technology for information storage, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server, a third-party computing device, a peripheral device, and/or the computing device. Combinations of any of the above also may be included within the scope of computer-readable media. The computer storage media, such as a database, provides storage of computer-executable instructions, data structures, program modules, and other data for the control, a third-party computing device, a peripheral device, and/or the computing device.

The control server may operate in a computer network using logical connection to one or more remote computers. Remote computers a third-party computing device, a peripheral device, and/or the computing device. Third-party computing devices may be associated with locations of third-party providers of various research related computing applications. The computers and computing devices may be personal computers, servers, routers, network PCs, peer devices, other common network nodes, personal digital assistants, smartphones, netbooks, tablet computers, or the like and may comprise some or all of the elements described above in relation to the control server. Peripheral devices may be devices with network, Bluetooth, or other connectivity.

Exemplary computer networks comprise local area networks (LANs) and/or wide area networks (WANs). Such networking environments are commonplace in offices, enterprise-wide computer networks, intranets, and the Internet. When utilized in a WAN networking environment, the control sever might comprise a modem or other means for establishing communications over the WAN, such as the Internet. In a networked environment, program modules or portions thereof may be stored in association with the control server, a database associated with the control server, or any of the computers/computing devices. In one example, various application programs may reside on memory associated with any of the computers/computing devices. The network connections shown are merely exemplary and other means of establishing communications linkages between the computers, computing devices, and control server may be utilized.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Synonymous codon substitutions change the translation rate at specific positions within an mRNA's coding sequence. An exemplary embodiment of the present invention was tested in silico by designing translation-rate profiles that accurately control the co-translational profile generated from coarse-grained (CG) molecular dynamics simulations of protein synthesis. For the in silico testing, the exemplary protein used was the single-domain MIT protein fused at its carboxy terminus to an unstructured polyglycine linker.

One of the necessary inputs for the system is a target co-translational profile, which consists of a list of state probabilities as a function of nascent chain length. In the case of the MIT protein those state probabilities are denoted, $P_U^{tar}(j)$, $P_I^{tar}(j)$, $P_F^{tar}(j)$, for the unfolded, intermediate, and folded state, respectively, at codon position j. To produce a folding-optimized mRNA sequence using the system, first an initial mRNA sequence is supplied, then a new sequence is generated by synonymously mutating a codon at a randomly selected position. The resulting co-translational profile of this new mRNA sequence, as predicted by the master step of this Example, is compared to the target co-translational profile by the energy term:

$$E(\text{new}) = \sum_{j=1}^{NC} |P_U^{tar}(j) - P_U^{new}(j)| + |P_I^{tar}(j) - P_I^{new}(j)| + |P_F^{tar}(j) - P_F^{new}(j)| \quad \text{(Equation 2)}$$

where $P_U^{new}(j)$, $P_I^{new}(j)$, $P_F^{new}(j)$, are the steady-state probabilities of the MIT domain populations in unfolded, intermediate, and folded states, respectively for the new mRNA sequence. The "tar" superscript indicates these are the user-defined target values. In the above equation, $N_c$ is the number of codons in the coding sequence of the mRNA.

$$P(j,t) = \begin{bmatrix} P_1(j,t) \\ P_2(j,t) \\ \vdots \\ P_N(j,t) \end{bmatrix} \quad \text{(Equation 6)}$$

and $$Mj = \begin{bmatrix} -\left(\omega_1(j+1) + \sum_{l=2}^{N} k_{1l}\right) & k_{12}(j) & \cdots & k_{N1}(j) \\ k_{12}(j) & -\left(\omega_2(j+1) + \sum_{l=1,l\neq 2}^{N} k_{2l}\right) & \cdots & k_{N2}(j) \\ \vdots & \cdots & \ddots & \vdots \\ k_{N1}(j) & \cdots & \cdots & -\left(\omega_N(j+1) + \sum_{l=1}^{N-1} k_{2l}\right) \end{bmatrix} \quad \text{(Equation 7)}$$

and $$T(j) = \begin{bmatrix} -\omega_1(j) & 0 & \cdots & 0 \\ 0 & -\omega_2(j) & \cdots & 0 \\ \vdots & \vdots & \ddots & \vdots \\ 0 & 0 & \cdots & -\omega_N(j) \end{bmatrix} \quad \text{(Equation 8)}$$

Larger E(new) values correspond to greater deviations between these two co-translational profiles. Therefore, the overall aim of the present invention is to identify the translation-rate profile that minimizes the energy term E(new).

The determination of whether to accept or reject the new mRNA sequence as described above, utilizes the Metropolis criterion by calculating the quantity:

$$E_\Delta = E(\text{new}) - E(\text{old}) \quad \text{(Equation 3)}$$

where E(old) is the energy associated with the old mRNA sequence. If $E_\Delta < 0$ then the new mRNA sequence is accepted and replaces the old sequence. However, if $E_\Delta > 0$, the new mRNA sequence is accepted with probability:

$$e^{-E_\Delta/T} \quad \text{(Equation 4)}$$

This process is then repeated 12 million times and yields converged results. The temperature of the previous equation effects the probability of accepting the new mRNA sequence when $E_\Delta > 0$. The example was conducted using a simulated annealing temperature schedule starting with T=10K and ending at $T \leq 2.4 \times 10^{-8}$. Every 60,000 Monte-Carlo steps, the system was quenched to a lower temperature by multiplying the current temperature by a factor of 0.99.

The master equation step was tested to determine if it is accurate enough to predict the impact of changing codon translation rates at specific mRNA position. This step includes an analytical expression for the steady-state probability that a protein will be in any one of N different states at each and every nascent chain length during its synthesis. The probability that a nascent chain of length j is in state k at time t is denoted by $P_k(j,t)$ where $k=\{1, 2 \ldots N\}$. The master equation governing the time evolution of these state probabilities of this system can be written as:

$$\frac{dP(j,t)}{dt} = M(j)P(j,t) - T(j)P(j-1,t) \quad \text{(Equation 5)}$$

where P(j,t) is a column vector of state probabilities:

M(j) and T(j) are N×N-size transition matrices describing the transitions between state in the nascent protein. In the expressions for M(j) and T(j), $\omega_k(j+1)$ is the rate at which $j^{th}$ codon is translated when the nascent chain is in state k and $k_{il}(j)$ is the rate of transitioning from state i to state l at codon position j. Solving the master equation at steady state conditions results in the recursive relation $$P(j) = M(j)^{-1} T(j) P(j-1) \quad \text{(Equation 9)}$$

That is, the steady-state probabilities (P(j)) at codon j depend on what happened at all earlier codon positions (P(j-1)). The elements of P(j) are denoted as $P_1(j), P_2(j), \ldots, P_{N-1}(j)$ and $P_N(j)$. Translation, in this model, involves an open system; therefore, the sum of the probabilities of populating different states at codon position j is not equal to one. For this reason, we then normalized these probabilities at each codon position by dividing the term $\Sigma_{i=1}^{N} P_i(j)$.

In order to achieve control the co-translational profile of a protein, the present system optimizes the mRNA sequences for a given co-translational profile. The overall aim of the system is to construct the mRNA sequence which produces such co-translational profile. For example, if one wants to use this framework to minimize the fraction of aggregated or non-functional protein, then an appropriate input co-translational profile should be supplied which minimizes the production of aggregated proteins. After obtaining the mRNA sequence, coarse-grained simulations were run on these mRNA sequences and the co-translational profiles from the simulation were calculated.

The steady state co-translational profiles obtained from the molecular dynamics simulation trajectories of the continuous translation on the optimized mRNA sequence were calculated according to the following formula:

$$P_i(j) = \frac{\sum_{k=1}^{N_{Traj}} \left[ \sum_{l=1}^{N_{Frames}(k,j)} \delta_{(i,j,l,k)} / \sum_{l=1}^{N_{Frames}(k,j)} 1 \right]}{\sum_{k=1}^{N_{Traj}} 1} = \frac{\sum_{k=1}^{N_{Traj}} P_{i,k}(j)}{\sum_{k=1}^{N_{Traj}} 1}$$ (Equation 10)

where $P_i(j)$ is the steady state probability of being in state i at codon j; $\delta_{(i,j,l,k)}$ is Kronekar-delta that equals 1 when the system is in state i at codon j in frame l of trajectory k. The summations are over the $N_{Traj}$ independent synthesis trajectories for a given translation rate profile, and the $N_{Frames}(k,j)$ saved during simulation trajectory k at codon j. In the above equation $P_{i,k}(j)$ is the probability of being in state i, at codon j in trajectory k.

Provided that M(j) is known, the above equation can be used to predict how the co-translational profile of protein changes due to changes in individual codon translational rates.

The accuracy of the above equation is tested by utilizing coarse-grained simulation data of the synthesis of a single-domain protein, known as MIT that is C-terminally fused to an unstructured linker. The coarse-grained simulation model explicitly includes the large ribosomal sub-unit and the nascent chain, which, at full length, is composed of a 43-residue poly-glycine linker covalently attached to the C-terminus of the single-domain MIT protein. This protein synthesis was simulated by E. coli's 50 S ribosomal subunit during continuous and arrested translation. In the coarse-grained model, amino acids were represented by a single interaction site. A +1e charge was assigned to interaction sites representing Lysine and Arginine resides and a -1e charge was assigned to the sites representing Glutamine and Aspartate residues. Other residues were assigned zero charge. Purine and pyrimidine nucleotides in the ribosomal RNA were represented by three and four interaction sites that represent, respectively the ribose ring, the phosphate group and each conjugated ring in the base. The CG interaction sites were positioned at the geometrical centers of these groups. The interaction site representing the phosphate group was assigned a charge of -1e.

The course-grained force field is the sum of five different energy terms:

$$E_{tot} = E_{bond} + E_{angle} + E_{dihedral} + E_{elec} + E_{LJ}$$ (Equation 11)

The first four terms in the above equation account, respectively, for bond energy, bond angle, dihedral angle, and pairwise electrostatic interactions, where:

$$E_{bond} = \Sigma_i \ K_b(r_i - r_0)^2$$ (Equation 12)

$$E_{angle} = \Sigma_i \ \exp(-\gamma K_\alpha(\theta_i - \theta_\alpha)^2 + \epsilon_\alpha) + \exp(-\gamma K_\beta(\theta_i - \theta_\beta)^2)$$ (Equation 13)

$$E_{dihedral} = \Sigma_{i,j} \ K_{\psi,j}(1 + (\cos(j\psi - \delta_{ij})))$$ (Equation 14)

$$E_{elec} = \Sigma_{i,j} \frac{q_i q_j}{4\pi\epsilon_0 \epsilon_r r_{ij}} \exp\left(-\frac{r_{ij}}{\ell_D}\right)$$ (Equation 15)

are fully transferable between different protein and RNA molecules. $K_b$ is the bond force constant; $(r_i - r_0)$ is the distance of an interaction site from its equilibrium positions; $\theta_\alpha$ and $\theta_\beta$ are the location of two minima on the angle-energy surface and their angle force constants are $K_\alpha$ and $K_\beta$, respectively; $\epsilon_\alpha$ is used to tune the relative balance between these two bond-angle energy minima; $K_\psi$ is the dihedral force constant; j is the multiplicity of the function; $\psi$ is the dihedral angle; and $\delta$ is the phase shift. For purposes of simulation, a Debye length $(l_D)$ of 10 Å[28] and a dielectric constant $(\epsilon_r)$ of 78.5.

The term $E_{LJ}$ incorporates structure-dependent van der Waals interactions. Utilizing Go's approach that treats the native interactions as attractive and non-native interactions as repulsive in a modified Lennard-Jones energy term, which accounts for desolvation barriers, the following equation is developed:

$$E_{LJ} = \Sigma_{i,j} \ \epsilon_{ij}\left[13\left(\frac{\sigma_{ij}}{r_{ij}}\right)^{12} - 18\left(\frac{\sigma_{ij}}{r_{ij}}\right)^{10} + 4\left(\frac{\sigma_{ij}}{r_{ij}}\right)^{6}\right]$$ (Equation 16)

The Lennard-Jones well depth $(\epsilon_{ij})$ between interaction states i and j that form native contacts in MIT protein was set equal to the values of the Bentancourt-Thirumalai statistical potential, and scaled by a multiplicative factor to achieve a realistic native native-state stability for the MIT protein. All other Lennard-Jones interactions were treated as effectively short-ranged and repulsive by setting their well depth equal to 0.000132 kcal/mol as in the Karanicols-Brooks model. The collision diameter $(\sigma_{ij})$ for the two interaction sites of the MIT protein is their distance in the crystal structure divided by two to the one-sixth power. Collision diameters for the intra-linker interactions were calculated according to Oh et al. (Selective Ribosome Profiling Reveals the co-translational chaperone action of trigger factor in vivo. *Cell* 147 12951308 (2011), incorporated herein by reference). The interaction between the polyglycine and MIT domain, ribosome and MIT domain, and ribosome and linker is defined as:

$$\sigma_{ij} = \frac{\sigma_i + \sigma_j}{2}$$ (Equation 17)

During the simulations, the ribosome is held rigid, therefore there are no terms representing bonded interactions in the force-filed for the RNA molecules. Specifically, arrested ribosome simulations of this ribosome nascent chain construct were analyzed and the rate matrix M(j) was computed at various nascent chain lengths.

In order to identify the three different states MIT can populate during the simulations, Markov state definitions were assumed. Specifically, the fraction of native contacts between helices 1 and 2 $(Q_{12})$ and between helix 3 and helices 1 and 2 $(Q_{12\text{-}3})$ were used, where $$Q_{1-2} = \frac{n_{12}}{n_{12}^c} \quad \text{(Equation 18)}$$

and $$Q_{12-3} = \frac{n_{12-3}}{n_{12-3}^c} \quad \text{(Equation 19)}$$

The six optimized mRNA sequences (shown in FIG. 4) are set out in Table 3. Fast, medium and slow translating codons are denoted by F, M and S, respectively.

TABLE 3

Figure 4A:
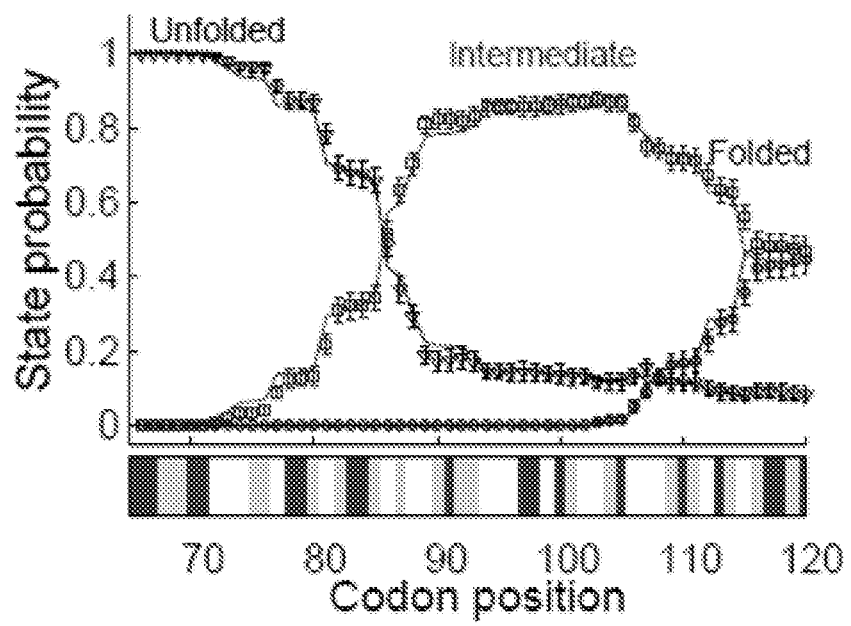
FIG. 4(a-f) shows the probabilities of populating the unfolded, intermediate and folded states of the MIT domain, plotted against the nascent chain length for six different optimized codon sequences ((a)-(f)) produced according to the invention. Unfolded=triangles; intermediate=squares; folded=circles, respectively. The user-defined target co-translational profiles are plotted as solid lines, while the discrete data points were obtained from the coarse-grained simulations of the continuous translation process from the optimized mRNA sequences generated by the present invention. Simulation data are plotted with error bars representing the 95% confidence interval. At the bottom of these panels, translation rate profiles of the optimized mRNA sequences are shown; dark areas represent fast translating codons, white areas represent slow translating codons, and medium grey areas represent medium-speed translating codons. The lowest $R^2$ values among the unfolded, intermediate and folded state probability curves in panels (a)-(f) are, respectively, 0.993, 0.962, 0.979, 0.947, 0.981 and 0.653. For all curves, p-values are less than 0.001
Figure 4B:
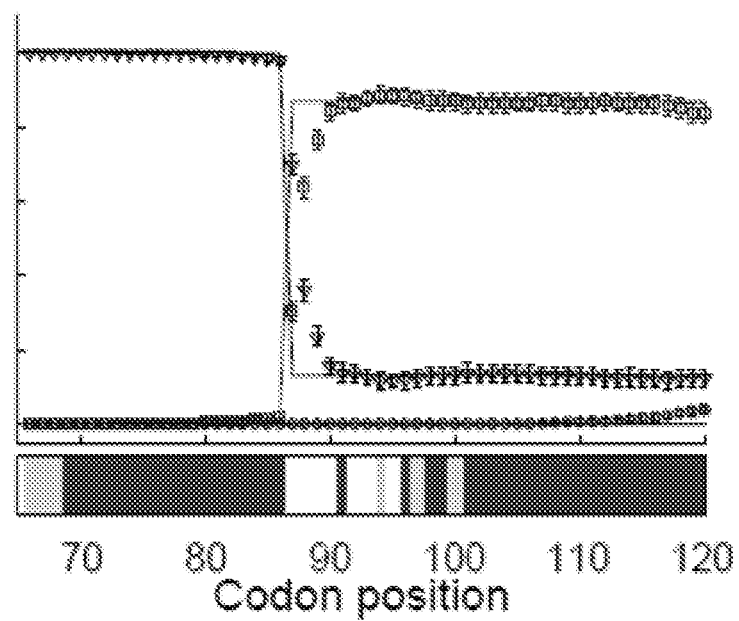
Figure 4C:
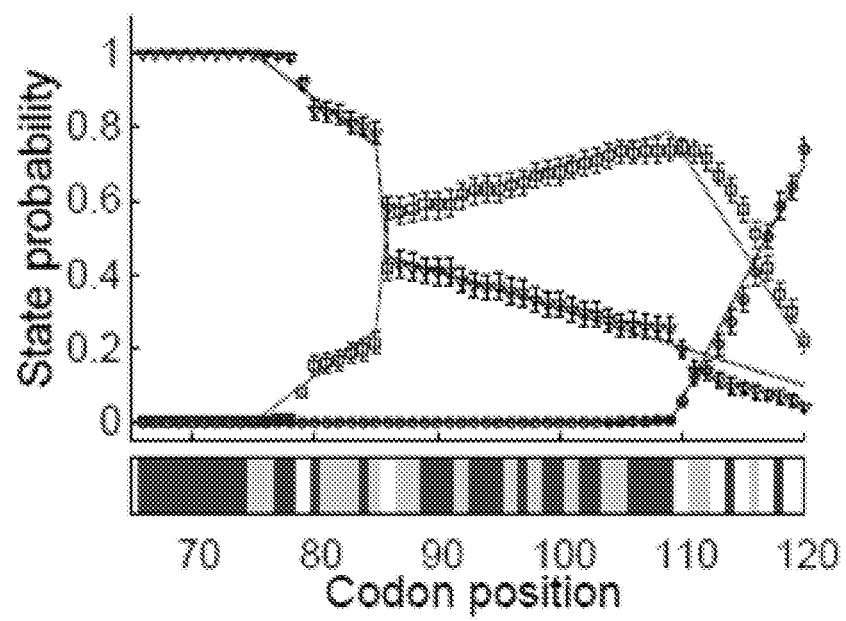
Figure 4D:
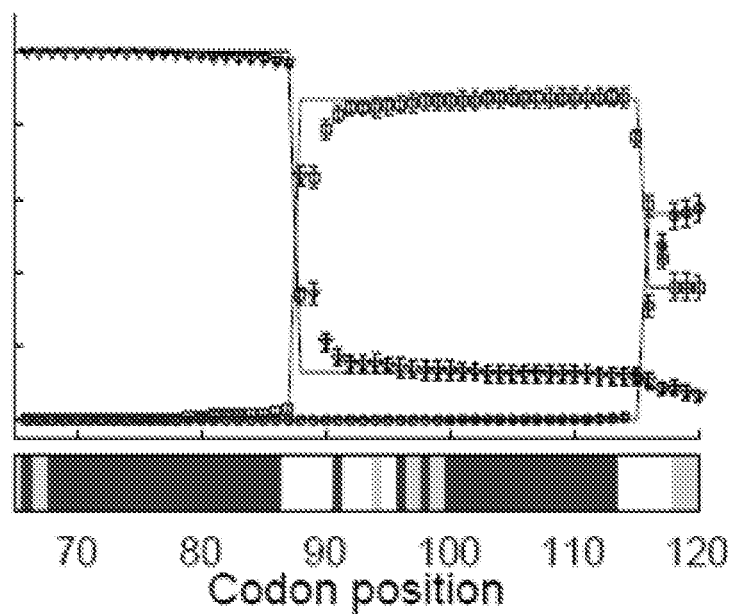
Figure 4E:
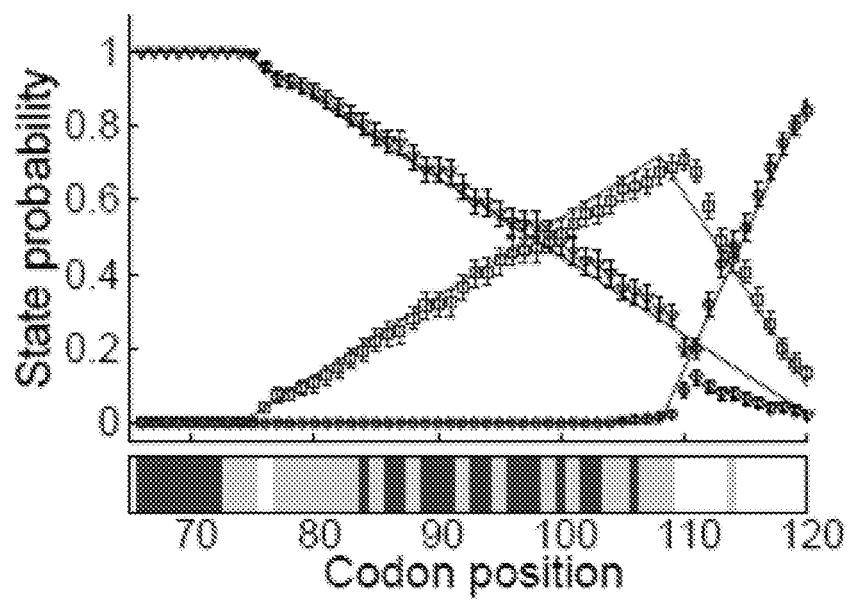
Figure 4F:
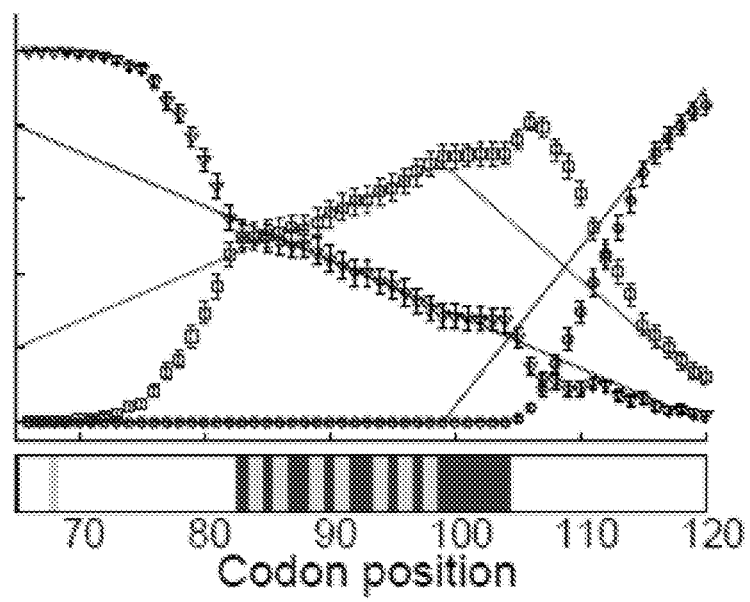
Figure 5:
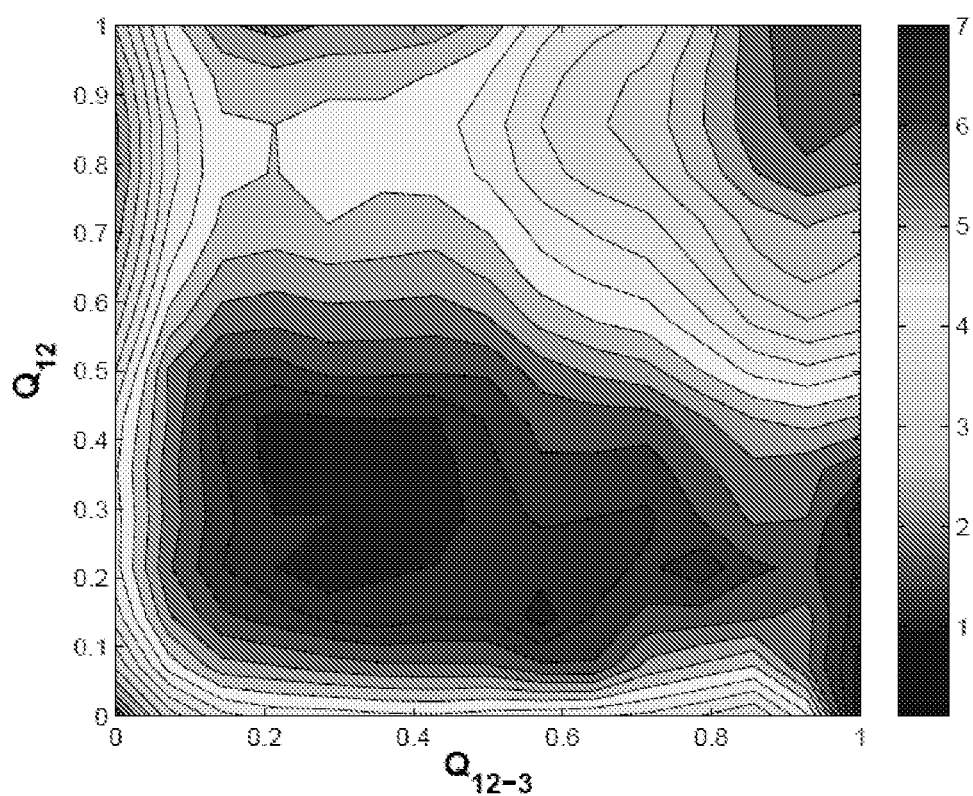
FIG. 5 shows an iso-contour map of the free energy landscape of MIT protein at 320 K is shown as a function of order parameters $Q_{12}$ and $Q_{12-3}$.

| Codon positions | Translation-rate profiles | | | | | |
|---|---|---|---|---|---|---|
| | FIG. 4(a) | FIG. 4(b) | FIG. 4(c) | FIG. 4(d) | FIG. 4(e) | FIG. 4(f) |
| 65 | F | S | S | M | S | F |
| 66 | F | M | F | M | F | S |
| 67 | F | M | F | F | F | S |
| 68 | M | M | F | F | F | M |
| 69 | M | F | F | F | S | S |
| 70 | F | F | F | F | F | S |
| 71 | F | F | F | F | F | S |
| 72 | S | F | F | F | F | S |
| 73 | S | F | F | F | M | S |
| 74 | S | F | F | F | M | S |
| 75 | M | F | M | F | M | S |
| 76 | M | F | M | F | S | S |
| 77 | S | F | F | F | M | S |
| 78 | F | F | F | F | M | S |
| 79 | F | F | S | F | M | S |
| 80 | M | F | F | F | M | S |
| 81 | S | F | M | F | M | S |
| 82 | M | F | M | F | M | S |
| 83 | F | F | M | F | M | F |
| 84 | F | F | F | F | F | M |
| 85 | M | F | M | F | M | F |
| 86 | S | F | S | F | F | M |
| 87 | M | S | M | F | F | F |
| 88 | S | S | M | S | M | F |
| 89 | S | S | F | S | F | M |
| 90 | M | S | F | S | F | F |
| 91 | F | F | F | S | F | M |
| 92 | M | S | M | S | M | F |
| 93 | M | S | F | S | F | F |
| 94 | S | M | F | M | F | M |
| 95 | S | S | F | S | M | F |
| 96 | S | F | M | F | F | M |
| 97 | F | M | F | M | F | F |
| 98 | F | F | M | F | F | M |
| 99 | S | F | F | M | M | F |
| 100 | F | M | F | M | F | F |
| 101 | M | F | M | F | M | F |
| 102 | S | F | F | F | F | F |
| 103 | S | F | F | F | F | F |
| 104 | M | F | M | F | M | F |
| 105 | F | F | M | F | M | S |
| 106 | S | F | F | F | F | S |
| 107 | S | F | F | F | M | S |
| 108 | S | F | F | F | M | S |
| 109 | M | F | F | F | M | S |
| 110 | F | F | S | F | S | S |
| 111 | M | F | M | F | S | S |
| 112 | S | F | M | F | S | S |
| 113 | F | F | S | F | S | S |
| 114 | M | F | F | F | M | S |
| 115 | S | F | S | S | S | S |
| 116 | M | F | M | S | S | S |
| 117 | F | F | S | S | S | S |
| 118 | F | F | F | M | S | S |
| 119 | M | F | S | M | S | S |
| 120 | F | S | S | M | S | S |

In the above equations, $n_{12}$ and $n_{12-3}$ are the number of native contacts formed by helix 1 with 2 and helix 3 with helices 1 and 2 in a given ribosome-nascent chain conformation; while $n_{12}^c$ and $n_{12-3}^c$ are the number of the native contacts between these structural elements in the crystal structure. The free energy surface of the MIT protein as a function $Q_{12}$ and $Q_{12-3}$ reveals three basins which correspond to the unfolded, intermediate, and folded states of the MIT protein as shown in FIG. 4. A conformation is identified in a particular fashion according to Table 1.

TABLE 1

| Conformation Identification | | |
|---|---|---|
| Folded | $Q_{1-2} > 0.85$ | $Q_{12-3} > 0.85$ |
| Intermediate | $0.95 > Q_{1-2} > 0.75$ | $Q_{12-3} < 0.05$ |
| Unfolded | $Q_{1-2} < 0.05$ | $Q_{12-3} < 0.05$ |

Table 2, below, shows the accuracy of the present system by comparing the input co-translational folding curves and co-translational folding curves obtained by using the optimized mRNA sequences.

TABLE 2

| R2-values and p-values for each curve shown in FIG. 4. | | | |
|---|---|---|---|
| FIG. | $P_U$ | $P_I$ | $P_F$ |
| 4(a) | $R^2 = 0.997$ | $R^2 = 0.993$ | $R^2 = 0.995$ |
| | $p \leq 0.001$ | $p \leq 0.001$ | $p \leq 0.001$ |
| 4(b) | $R^2 = 0.961$ | $R^2 = 0.961$ | NA |
| | $p \leq 0.001$ | $p \leq 0.001$ | NA |
| 4(c) | $R^2 = 0.991$ | $R^2 = 0.979$ | $R^2 = 0.993$ |
| | $p \leq 0.001$ | $p \leq 0.001$ | $p \leq 0.001$ |
| 4(d) | $R^2 = 0.967$ | $R^2 = 0.957$ | $R^2 = 0.947$ |
| | $p \leq 0.001$ | $p \leq 0.001$ | $p \leq 0.001$ |
| 4(e) | $R^2 = 0.991$ | $R^2 = 0.981$ | $R^2 = 0.995$ |
| | $p \leq 0.001$ | $p \leq 0.001$ | $p \leq 0.001$ |
| 4(f) | $R^2 = 0.950$ | $R^2 = 0.653$ | $R^2 = 0.920$ |
| | $p \leq 0.001$ | $p \leq 0.001$ | $p \leq 0.001$ |

The conformations not belonging to any of these states are in the transition region. If a simulation trajectory enters the transition region the most recent state visited by the trajectory is assigned to these conformations. This type of "core-based" partitioning of free energy surface can accurately capture the essential kinetics in molecular dynamics simulations.

Rate matrices were calculated from the time-series of different states acquired by the protein during the CG simulation. It was assumed that a protein can populate N different states at nascent chain length j. Then assuming transitions between states are Markovian as described above, the first passage time distribution of transitioning out of a state i to any other state will decay exponentially as $$f(i) = \exp(-k(i)t) \quad \text{(Equation 20)}$$

where $$k(i) = \sum_{l=1, l \neq i}^{N} k_{il} \quad \text{(Equation 21)}$$

In the above equation, $k_{il}$ is the rate of transitioning from state i to l. Therefore k(i) is the sum of the rates leading to all topologically connected states from state i. Moreover, if $n(i \rightarrow l)$ is the total number of transitions from state i to l observed during the simulations, then $$\frac{n(i \to l)}{\sum_{m=1, m \neq i}^{N} n(i \to m)} = \frac{k_{il}}{\sum_{m=1, m \neq i}^{N} k_{im}} \quad \text{(Equation 22)}$$

For an N-state protein, there are N−2 independent equations of the same form as the above equation. Solving the prior two equations for $k_{il}$ determines the N−1 transition rates leading to any state from state i. In order to calculate these for MIT, the arrested ribosome simulation trajectories were utilized. For each of these simulations trajectories, the time-series of Markov states were produced, as described above, which were then used to numerically calculated the various f(i) and n(i→l). A least-squares fit of the f(i) values was performed to a single exponential function and extracted the k(i) values were used to calculate the transition rates between states.

Figure 3:
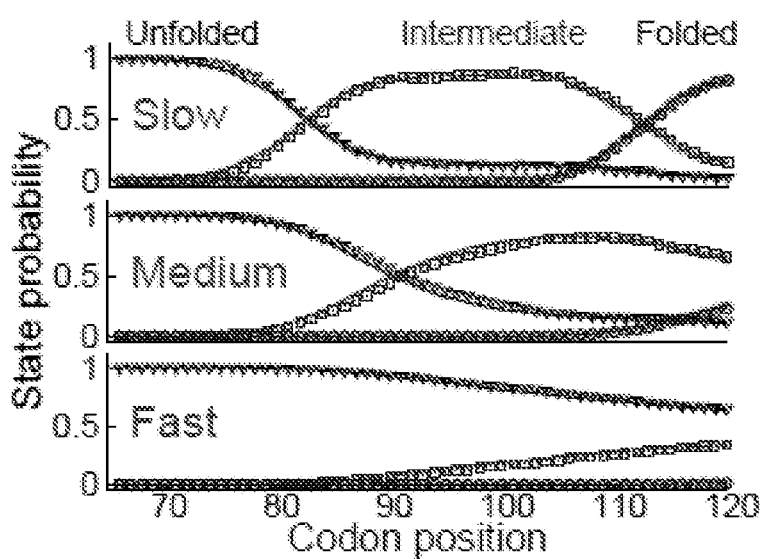
FIG. 3 indicates the steady state probabilities of the 77-residue MIT domain in the unfolded, intermediate, and folded states which are plotted against the nascent chain length, where unfolded is depicted with triangles, intermediate is depicted with squares, and folded is depicted with circles, on three globally homogeneous mRNA sequences consisting of only "slow," "medium," and "fast" translating codons. The solid lines are the numerical prediction made by the master equation approach and the gray area around these curves covers the 95% confidence interval of the numerical predictions.

These were then used in the master equation to predict how uniformly changing the translation rate at all codon positions altered the co-translational profile of this protein. These predictions were then tested against explicit, continuous synthesis simulations at those same global transition rates shown in FIG. 3. It was found that the predictions from the master equation were highly accurate, indicating that it is possible to predict the effect of changing codon translation rates on a protein's co-translational profile provide the M(j) is known. A similar or other method can be used to calculate the M(j) from such trajectories obtained by the FRET or other experiments.

Example 2

Having established that the method of Example 1 yields accurate results, this example was conducted to determine if the present invention could design translation-rate profiles to control co-translational folding. To do this for the MIT protein, six different co-translational profiles were first defined. Some of these profiles were irregular, including step function and linear-ramp behaviors. It was assumed that each codon position in the MIT's mRNA can either a fast, medium, or slow translating codon present. Thus, for this 120 residue protein, there are $3^{120}$ (~$10^{57}$) mRNA sequences that can encode its primary structure. Using the six different profiles as inputs to the method of Example 1, the six different optimized codon sequences of FIG. 4 were produced. As an explicit check that these six sequences actually control folding in the prescribed manner, Langevin dynamics simulations of continuous synthesis of the MIT protein using each of these optimized translation rate profiles were run and the resulting co-translational profiles were calculated.

The Charmm version c35b5 was used to run the Langevin dynamics simulations of the ribosome-nascent chain complex. An integration time step of 0.015 ps, a collision frequency of 0.05 ps$^{-1}$, and a system temperature of 310 K was used. For the continuous translation simulations, 1,200 independent trajectories were run for the fast and medium mRNA sequences, while 720 trajectories were simulated for all other cases. For the arrested ribosome simulations, 20 different Langevin dynamics simulations of the arrested ribosome-nascent chain complex at each codon position between 69 and 89 (inclusive) were run, and 8 independent trajectories at all other lengths. Different initial velocity distributions were used to initiate each trajectory. The ribosome was held rigid during the simulations by using the "cons fix" command of the constraint module in Charmm. This constraint has no significant effect on the thermodynamics and kinetics of co-translational protein folding because the ribosome exit tunnel does not exhibit any large scale fluctuations. System configurations were saved every 50 time steps in the simulations of continuous translation of the slow mRNA sequence, every 150 time steps for the optimized mRNA sequences and every 500 time steps for all other simulations. The MIT protein cannot populate the intermediate and folded states at codon positions 1 through 65, therefore the starting structure for all simulations consisted of a ribosome-nascent chain complex containing the 65 N-terminal residues of the protein. The procedure described in Caniparoli and O'Brien was used to stochastically add amino acids to the nascent chain. The dwell time of the ribosome at each codon position was exponentially distributed to mimic the addition of amino acids as a Markov process. Because the Langevin dynamics simulations were performed in the low friction regime, faster folding kinetics occurs as compared to experimental values. Therefore, to keep a reasonable ratio of the time scales of folding and translation the value of the translation rates was increased to 66.4 μs$^{-1}$, 664.0 μs$^{-1}$ and 6640.0 μs$^{-1}$ for the slow, medium and fast translating codons, respectively.

Example 3

Using the validated method of Example 1, the question of how many different synonymous mRNA sequences give rise to a particular co-translational profile and whether this degeneracy depends on the profile itself was addressed by calculation how many different mRNA sequences give rise to each of the five co-translational profiles shown in FIG. 4. This was done by running 32 independent Monte-Carlo trajectories and recorded each unique translation-rate profile that reproduced the optimized target profile to within a particular threshold of the quantity, E(MC$^j$), defined as:

$$E(MC^k) = \sum_{j=1}^{N_B} |P_U^{opt}(j) - P_U^{MC,k}(j)| + |P_I^{opt}(j) - P_I^{MC,k}(j)| + |P_F^{opt}(j) - P_F^{MC,k}(j)| \quad \text{(Equation 23)}$$

In the above equation, $P_U^{opt}(j)$, $P_I^{opt}(j)$, $P_F^{opt}(j)$, are the optimized steady state probabilities of the MIT domain being in states U, I, and F, respectively, whereas $P_U^{MC,k}(j)$, $P_I^{MC,k}(j)$, $P_F^{MC,k}(j)$, are the steady state probabilities for the k$^{th}$ random sequence generated by the method of Example 1. Thus, with this threshold, degenerate from non-degenerate sequences can be distinguished. As only the unfolded state of MIT can be populated at codon positions 1 through 69, any degeneracy arising from this region is ignored and instead focus is placed on the region between codon positions 70 to 120 as it is there that changing translation rates can alter the state that is populated.

It was found that the number of degenerate sequences depends on the co-translational profile and ranges from 84 to 13,359 for the five profiles tested. For all profiles, converged behavior is observed, consistent with an exhaustive search. Further evidence of an exhaustive search is that in the vast majority of Monte-Carlo trajectories, all the degenerate sequences are found within a single trajectory.

Example 4

An in silico synonymous codon scanning experiment in which single-point mutations were made at each and every codon position in the wild-type mRNA sequences and the effect on MIT's co-translational profile was calculated using the method of Example 1. This was done for each of the 5 optimized mRNA sequences shown in FIG. 4. The effect of a mutation as codon position j on the co-translational profile was measured as the root-squared-distance between the mutated and wild-type profile:

$$\chi(j) = \sqrt{\sum_{k=j}^{N_c} ((P_U^{org}(k) - P_U^{mut}(k))^2 + ((P_I^{org}(k) - P_I^{mut}(k))^2 + ((P_F^{org}(k) - P_F^{mut}(k))^2)}$$ (Equation 24)

In the above equation, $P_U^{org}$, $P_I^{org}$, $P_F^{org}$, are the steady-state probabilities of the MIT domain being in states U, I, and F, respectively, for the wild type sequence and $P_U^{mut}(k)$, $P_I^{mut}(k)$, $P_F^{mut}(k)$, are the steady state probabilities after the synonymous mutation was introduced. In this in silico experiment, there are two choices for the synonymous substitution at each codon position. Both possible types of single-point substitutions at each codon positions were carried out and the sensitivity ($\chi$) was calculated for each case. The distribution of sensitive codon positions and the most sensitive locations change depending on the starting co-translational profile as shown in FIG. 4. Between the two distributions the most sensitive codon positions switch from codon position 84 and 115, to 90. Thus, for the same protein, a synonymous codon substitution at position 84 may or may not have a significant impact on folding depending on the starting co-translational profile.

Example 5

Table 4, below, shows the number of Monte-Carlo runs that produced all possible degenerate sequences out of 32 independent runs, and the number of degenerate sequences for the five optimized mRNA sequences. To determine whether the number of mRNA sequences that give rise to the same co-translational profile (i.e., the profile's degeneracy) should be related to the sensitivity of the co-translational profile of the starting sequence to single-point synonymous substitutions, as single-point substitution profiles might not capture the combinatorial complexity, nor the additive and subtractive effects that multiple, simultaneous mutations could have, it was examined if there was a correlation between the number of degenerate sequences, shown in Table 4, and either the number of insensitive mutations or the number of insensitive codon positions. An insensitive mutation is defined as one in which a synonymous substitution into the optimized mRNA sequence causes no change in the co-translational profile with a threshold of E(mut)≤ 0.075. An insensitive codon position is one in which both alternative synonymous mutations at that position lead to no change in the co-translational profile.

TABLE 4

| Profile in FIG. | Number of Monte-Carlo runs that produced all degenerate sequences | Degenerate Sequences |
|---|---|---|
| 4(a) | 16 | 13,359 |
| 4(b) | 32 | 5,642 |
| 4(c) | 29 | 121 |
| 4(d) | 32 | 2,881 |
| 4(e) | 32 | 84 |

It was found that Pearson coefficients of greater than 0.91, with over 83% of the variance in degeneracy is explained by either one of the variables. Thus, there is strong support for the existence of a relationship between a co-translational profile sequence degeneracy and that profile's robustness to single-point synonymous mutations. The practical benefit of this is that it allows an experimentalist to take results from a synonymous-codon scanning experiment and get a sense of the degeneracy of the wild type co-translational profile.

Example 6

In order to determine whether codon positions that are most sensitive to a synonymous codon substitution are those that are furthest from equilibrium, $\Delta(j)$, a measure of the difference between the equilibrium co-translational profile and the wild-type co-translational profile at codon position j and downstream positions was defined as:

$$\Delta(j) = \sqrt{(N_c - j + 1)((P_U^{org}(j) - P_U^{eq}(j))^2 + ((P_I^{org}(j) - P_I^{eq}(j))^2 + ((P_F^{wt}(i) - P_F^{eq}(i))^2}$$ (Equation 25)

The equilibrium probabilities, $P_{i \in \{U,I,F\}}^{eq}$ are calculated under conditions in which translation is arrested ($\omega(j)=0$ at all j). A $\Delta(j)$ value of 0 means that the wild type and equilibrium profiles are the same starting at codon j and thereafter, $\Delta(j)>0$ means there are differences, with larger $\Delta(j)$ values exhibiting larger deviations from the equilibrium co-translational folding process.

A moderate to strong correlation between $\chi_{max}(j)$ and $\Delta(j)$ for all five co-translational profiles. For three out of five profiles, over 82% of the variance in codon position sensitivity can be explained by the deviation from equilibrium. For the other two profiles, 61% and 33% can be explained by $\Delta$. Thus, in the majority of cases for the MIT protein, simply comparing the wild-type and arrested-ribosome co-translational profiles provides an excellent predictor of which codon positions are likely to strongly influence co-translational folding upon a synonymous mutation.

Example 7

To further account for variance, and assuming a protein domain can only populate two possible states during translation, U and F, the rate of transitioning from the unfolded to folded states at nascent chain length j is denoted by $k_{UF}(j)$ and the reverse transition occurs with rate $K_{FU}(j)$. Then using the method of Example 1, it is found that:

$$P_F^i(j) = \frac{k_{UF}(j) + \omega^i(j+1)P_F^{wt}(j-1)}{k_{UF}(j) + k_{FU}(j) + \omega^i(j+1)}$$ (Equation 26)

where i∈{wt, mut}.

The change in the steady-state probability of the fold state at codon position j upon introducing a synonymous mutation is then $$P_F^{mut}(j) - P_F^{wt}(j) = A(P_F^{wt}(j) - P_F^{eq}(j)) \quad \text{(Equation 27)}$$

where $$C_{j+1,k} = \prod_{i=j+1}^{k} \frac{\omega^{wt}(i+1)}{\omega^{wt}(i+1) + k^{eq}(i)}$$

A is defined as below. Then inserting the above equation into the expression of χ(j) and Δ(j) for the last codon position yields:
a chemical kinetic model describing co-translational folding involving only two states, U and F to find the following relation between χ(j) and Δ(j) at the last codon of the coding sequence:

$$\chi(j) = |A|B\Delta(j) \quad \text{(Equation 29)}$$

where $$A = \frac{\left(\frac{\omega^{mut}(j+1) - \omega^{wt}(j+1)}{\omega^{wt}(j+1)}\right)}{\left(1 + \frac{\omega^{mut}(j+1)}{k^{eq}(j)}\right)} \quad \text{(Equation 30)}$$

where $$B = \sqrt{\frac{1 + \sum_{i=j+1}^{N_c} C_{j+1,i}}{N_c - j + 1}} \quad \text{(Equation 31)}$$

The parameter B determines how the change in a co-translational profile upon introducing a synonymous mutation propagates to subsequent codon positions and is bounded by 0 and 1 (0≤B≤1). A smaller B value indicates that the effect of a synonymous mutation will disappear or be significantly reduced after the translation of just a few downstream codon positions, whereas a large B value suggests the co-translational perturbation is propagated far downstream of the original mutation site.

The above equation is the characteristic time scale over which a non-equilibrium configuration decays to equilibrium at codon position j. $\tau^{wt}(j)$ and $\tau^{mut}(j)$ are the mean dwell times of the ribosome at codon position j for wild-type case and after synonymous mutation.

The foregoing Examples have demonstrated that a wide range of co-translational folding behaviors can be encoded in an mRNA sequence. For the MIT protein, which can populate an on-pathway, native-like intermediate, co-translational behavior was encoded in the state probabilities that displayed step-function (FIGS. 4(b) & 4(d)), linear-ramp (FIG. 4(e)) and a combination of step-function and linear-ramp (FIG. 4(c)) changes during synthesis. Reproduction of these profiles using the optimized mRNA sequences in independent coarse-grained simulations (FIG. 4) demonstrates the precision with which our framework can control the co-translational folding process.

In summary, the results set out in these Examples show that a co-translational profile's deviation from equilibrium, its sensitivity to single-point mutations, and its mRNA-sequence degeneracy are inter-related, and that each of these factors has direct implications for nascent protein behavior, critical codon positions and mRNA sequence evolution.

Example 8

All previous results were based on applying the sequence design method to the MIT domain simulated using a coarse-grained representation and low-friction Langevin dynamics—two modeling techniques known to artificially accelerate the rates of protein folding by orders of magnitude. For this reason, the codon translation rates were also accelerated in those synthesis simulations (see Methods). This raises the question of whether the conclusions drawn from MIT will hold for proteins that are modeled at more realistic, physiologically relevant rates.

To address this question we applied our method to domains from four different proteins from *E. coli* (SYK1, domain 1; TRXB, domain 3; FDHF, domain 4; AAT, domain 2) that were previously predicted to co-translationally fold. We used estimated codon translation rates for *E. coli* growing at 310 K and doubling every 150 min. In these estimates the 64 codons translate with rates that range from 2.5 to 54.0 AA/s. We used a previously published phenomenological model that predicts a domain's kFU(j) and kUF(j) values (eqs 38 and 39) on the ribosome based, in part, on the domain's size and structural class.

$$k_{UF}(j) = \frac{k_{UF}(\text{bulk})}{1 + ae^{-j+l+25} + \frac{b}{j^c}} \quad \text{(Equation 38)}$$

$$k_{FU}(j) = k_{FU}(\text{bulk})\left(\frac{1 + e^{-j+l+30}}{d}\right) \quad \text{(Equation 39)}$$

These models provided us with all the rates necessary to use our design framework. Thus, we did not need to use molecular simulations to obtain the interconversion rate matrix M(j) as we did for MIT.

It was found that for three out of the four of *E. coli* protein domains the methods of the present invention can find mRNA sequences that accurately reproduce user-defined profiles (FIG. 13). The algorithm did not work well for one of the domains (FIG. 13d). Thus, as with MIT, our algorithm works even at physiologically relevant rates of folding, unfolding, and codon translation.

It was also examined whether the biologically relevant findings from MIT also held for these proteins. Indeed they do: critical codon positions can shift depending on the co-translational profile as seen by plotting χmax vs j for the two co-translational profiles of FDFH protein (FIG. 13c). Mild to moderate correlations between χmax and Δ are observed for these proteins, indicating that the more sensitive a codon position is (i.e., the larger χmax) the more likely it is to be located at positions where the co-translational profile is further from the equilibrium profile. Also, tentatively, it was observe that, as with the MIT domain, the number of unique mRNA sequences that yield the same co-translational profile for TRXB protein depends on the original co-translational profile and likely spans almost an order of magnitude or more. The last observation is tentative because it is known that, despite best efforts, estimates of the number of degenerate mRNA sequences are not converged for all of the co-translational profiles associated with the TRXB protein. Unlike MIT, only for a minority of the 32 independent runs of our framework do we find the same unique sequences. This means the values are lower bounds of the true number of degenerate mRNA sequences. Because the numbers of degenerate sequences are not exact, we cannot test whether, like for MIT, the degeneracy correlates with the sensitivity to single-point synonymous mutations for these proteins. Thus, where the data permits rigorous testing, all of the conclusions drawn from these *E. coli* proteins are consistent with those from MIT.

Example 9

A chemical kinetic model was developed to predict the course of co-translational folding of proteins. First, the results were compared to experimentally-measured co-translational folding curves measured by pulse-chase experiments.

Only radiolabeled nascent chains are visible during these experiments, with un-labelled nascent chains making no contribution to the co-translational folding curve. Thus, only translation-initiation and elongation events that occur during the period of radiolabel incorporation contribute to the measured co-translational folding curve, as these events generate chains that are radiolabelled, while such translation events that occur outside the incorporation period do not.

From these considerations, it follows that the calculation of the experimentally-measured co-translational folding curve ($P_F(t)$) must account for (1) contributions from both ribosome-bound and ribosome-released radiolabeled nascent chains; (2) that at different time points during the experiment, the ribosome-bound population can contain sub-populations of nascent chains of different lengths; and (3) that the ribosome-released population can contain nascent chains that were released from the ribosome at different time points. The contribution to the co-translational folding curve from the ribosome-bound nascent chain population is proportional to the fraction of nascent chains that are both radiolabeled and folded at a nascent chain length of i, while the contribution from the ribosome-released nascent chains is proportional to the fraction of radiolabeled released nascent chains and the time since their release. These ideas are expressed mathematically as:

$$P_F(t) = \underbrace{\sum_{i=1}^{M} P_{F,B}(i) f_{L,B}(i, t)}_{\text{Contribution from ribosome-bound and labelled nascent chains}} + \underbrace{\sum_{t'=0}^{t} P_{F,R}(t, t') f_{L,R}(t, t')}_{\text{Contribution from ribosome-bound and labelled nascent chains}} \quad \text{(Equation 32)}$$

Figure 6A:
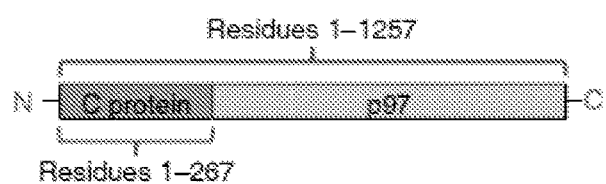
FIG. 6(a) shows a schematic representation of the relevant protein segments of WT SFVP.
Figure 6B:
FIG. 6(b) shows the crystal structures of the three protein segments studied for co-translational folding curves. The top left structure is the C protein of SFVP, the lower left is the FRB domain, and the structure to the right is HA1.

The first summation term in Equation 31 represents the contribution of ribosome-bound, labeled chains to the co-translational folding curve, and the second term is the contribution from released, labeled chains. In equation (1), $P_{F,B}(i)$ is the probability that the nascent chain segment of interest (that is, the segment whose folding is being monitored) is folded (F) and bound (B) to the ribosome at a nascent chain length of i. The nascent chain segment of interest for SFVP is C protein (FIG. 6a). $f_{L,B}(i, t)$ is the fraction of ribosome-bound (B) nascent chain segments of interest that are at codon position i and contain a radioactive label (L) at time t. A nascent chain segment is considered radiolabeled if at least one residue in the segment of interest is labeled. Although the absolute intensity of the phosphorimaging signal is directly proportional to the number of radioactive amino acids in a peptide, Helenius and co-workers normalized the experimental data by dividing by the maximum observed intensity. This normalization procedure removes the signal's dependence on the absolute number of radiolabeled amino acids and absolute number of labeled protein molecules, yielding the co-translational folding probability. $P_{F,R}(t, t')$ is the probability that at time t the nascent chain segment of interest is folded (F) for those nascent chains released (R) from the ribosome at time t', where $0 \le t' \le t$. $f_{L,R}(I)$ is the fraction of labeled (L) nascent chains at time t that were released (R) from the ribosome at time t'. The first summation in equation (1) is over the different nascent chain lengths (from codon i=1 to i=M, the stop codon) and the second summation is over the different time points during the experiment.

To determine mathematical expressions for each of the terms in equation (1), the following assumptions were made:

A1. That steady-state translation kinetics occur throughout the time course of the experiment, which requires that the number of ribosomes initiating translation is equal to the number of ribosomes terminating translation at all times during the experiment. Consistent with this assumption, Applicants performed Ribo-seq experiments on yeast and found that, for genes that have good coverage, stationary ribosome profile distributions occur between biological replicates. Furthermore, the constant rate of accumulation of full-length SFVP during the pulse-chase experiment means that the rate of protein synthesis is constant; this can only be the case if translation is occurring at steady state.

Figure 7:
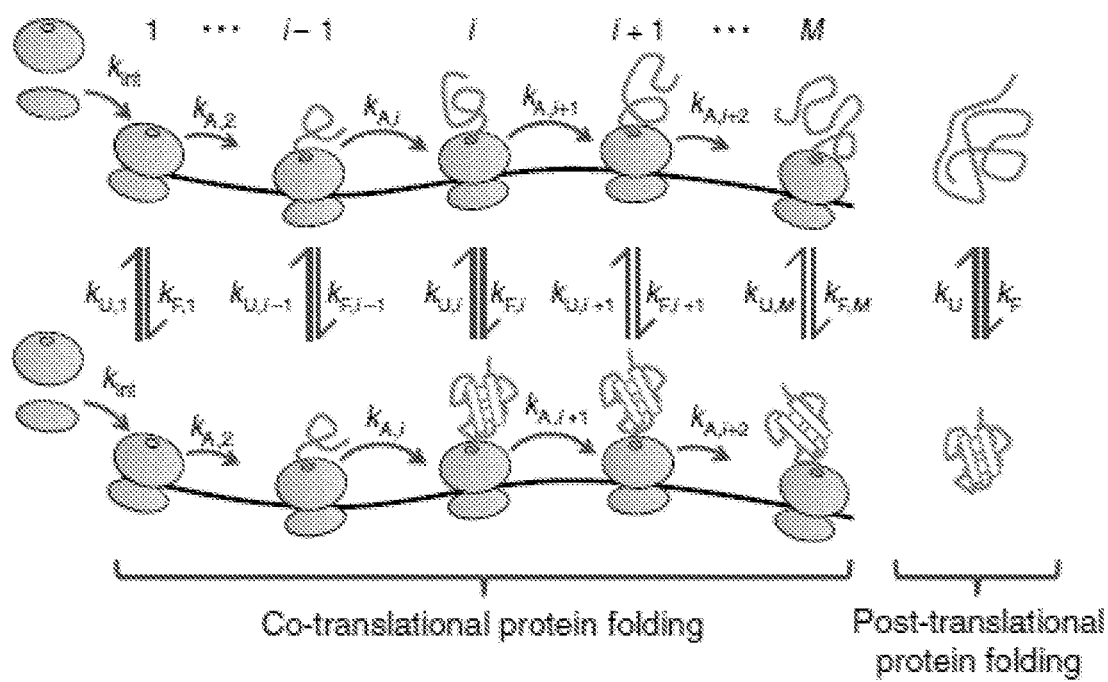
FIG. 7 shows the co- and post-translational protein folding reaction scheme that equation (32) solves.

A2. That the co- and post-translational folding of the nascent chain segment of interest occurs in a two-state manner (FIG. 7), with rates $k_{U,i}$ and $k_{F,i}$ at nascent chain length i, and rates $k_U$ and $k_F$ for ribosome-released nascent chains. Two-state folding indicates that the nascent chain segment does not populate any intermediate states, which is a reasonable assumption for small, cooperative folding domains. C protein has been shown to fold in a manner consistent with this two-state assumption.

A3. That the dwell time of the ribosome at a particular codon position is exponentially distributed, with the rate of translation of codon i denoted $k_{A,i}$.

Under assumptions A1-A3, and with the introduction of discretization of t into time points of duration $s\delta t$, equation (1) can be rewritten as:

$$P_F(t(s)) = \frac{1}{\sum_{i=1}^{M} N_{L,B}(i, t(s)) + \sum_{n=0}^{s} N_{L,R}(t(s), t'(n))} \quad \text{(Equation 33)}$$

$$\left[ \sum_{i=1}^{M} N_{L,B}(i, t(s)) P_{F,B}(i) + \sum_{n=0}^{s} N_{L,R}(t(s), t'(n)) \left( \left[ P_{F,B}(M) - \frac{k_F}{k_F + k_U} \right] e^{-[k_F + k_U][t(s) - t'(n)]} + \frac{k_F}{k_F + k_U} \right) \right],$$

A concern with any model that aims to predict experimentally-measured quantities is that it will be under constrained. In such situations it is common to introduce additional assumptions to reduce the number of free parameters. Equation 32, with only assumptions A1, A2 and A3, is an under-constrained model for predicting SFVP's behavior, as 3,771 rates are needed. These rates are the 1,257-codon translation rates in the CDS, and C protein's folding and unfolding rate at each of the 1,257-nascent chain lengths. However, introducing three additional assumptions results in a fully constrained model.

A4. That each codon translates at the average codon translation rate. There is experimental evidence that this is a reasonable approximation for some proteins. While it is almost certainly the case that translation rates can vary from one codon to the next, it has been shown in mouse stem cells that no matter the length or type of protein being translated, all proteins are translated with an average codon translation rate of 5.6 AA per second. On heuristic grounds, it is expected that this experimental observation likely arises from the Central Limit Theorem, meaning that the most-probable codon translation rate will be the average codon translation rate provided that these rates are randomly distributed across the CDS.

A5. That the nascent chain segment of interest is only sterically permitted to fold once it emerges from the ribosome exit tunnel. This assumption is supported by structural, proteolysis, single molecule and coarse-grained simulation studies that demonstrate that protein domains need linker lengths of between 24 and 40 residues to fold, as the exit tunnel is too narrow to allow large domains to fold.

A6. That once C protein is sterically permitted to fold and unfold it does so at its bulk folding and unfolding rates. Coarse Grained simulations of protein-G folding on the ribosome found it attained its bulk folding and unfolding rates just three residues beyond the nascent chain length at which it could form a thermodynamically-stable folded structure. A single-molecule experiment suggests that T4 lysozyme attains its bulk folding and unfolding rates at a linker length of 80 residues, 40 residues after it has emerged from the exit tunnel. Consider that C protein is sterically permitted to fold starting at 297 residues in length, such that at nascent chain lengths between 297 and 337 residues its $k_F$ and $k_U$ may differ from their bulk values. From 337 to 1,257 residues in length, however, C protein has most likely attained its bulk $k_F$ and $k_U$ values. Thus, for only 40 out of 920 (=1,257-337) nascent chain lengths are the $k_F$ and $k_U$ of C protein potentially different than its bulk values, or only 4% of the nascent chain lengths at which C protein is sterically permitted to fold. This assumption is therefore reasonable for the proteins investigated.

Assumption A4 reduces the number of required translation rates from 1,257 to 1, reducing the number of required parameters by 1,256. Assumption A5 reduces the number of free parameters by 592 (=2×296), because the $k_{U,i}$ and $k_{F,i}$ values for i≤296 residues can be set to 0 s$^{-1}$. Assumption A6 reduces the number of free parameters by 1,920 (=2×(1, 256–296)), as for all nascent chain lengths at which folding and unfolding are permitted the bulk $k_F$ and $k_U$ values are used. Thus, with these assumptions, only three parameters are required to make predictions using Equation 32: the bulk $k_F$ and $k_U$ values and average $k_A$. Therefore, the predictions are made based on a model that is fully constrained by literature reported values.

Example 10

Figure 8A:
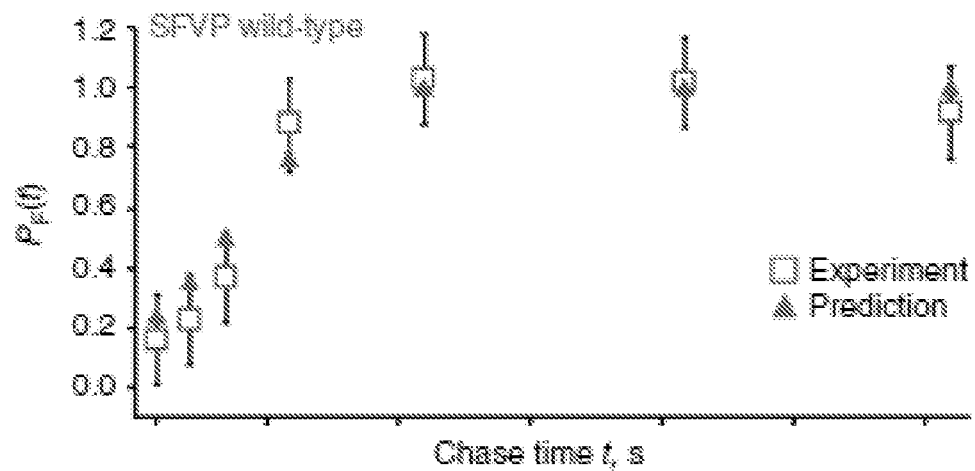
FIG. 8(a-b) shows the comparison between predicted and experimentally measured SFVP co-translational folding curves for wild type (a) and AC mutants (b) of SFVP.
Figure 8B:
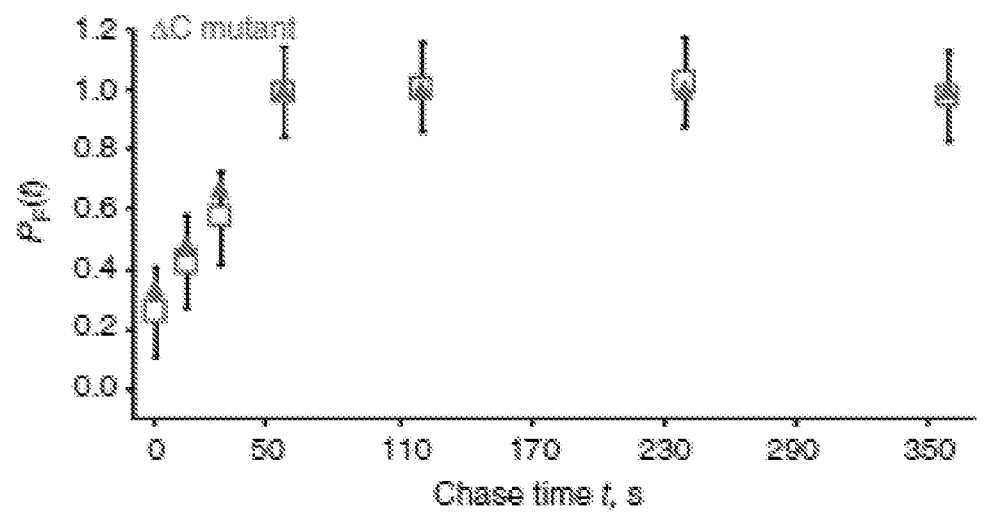

Using as input parameters the experimentally-determined values of $k_F$, $k_U$ and $k_A$ for C protein in CHO cells and the experimental values of a 45-s pulse period and a 360-s chase period, with a 10-s delay in the start of the incorporation period as is observed to occur in CHO cells, we find that Equation 32 accurately predicts the experimentally measured co-translational folding curves for both the WT and ΔC SFVP constructs (FIG. 8).

As a further test of the approach, the Inventors also modelled in vivo co-translational folding curves for the 99-amino acid FKBP12-rapamycin-binding domain of a Flag-FRB-GFP construct and the 290 structured residues of the viral protein HA1 from influenza A/PR8. These co-translational folding curves have been measured using the experimental technique known as folding-associated co-translational sequencing (FactSeq). FactSeq is a Next-Gen sequencing technique that uses substrate or antibody binding to monitor the co-translational folding status of a protein segment as a function of the nascent chain length rather than as a function of time as in pulse-chase measurements. Thus, equation (34A) and not equation (33) is appropriate for predicting these co-translational folding curves. For FRB and HAL we used the $k_F$ and $k_U$ values reported in Table 1.

$$P_{F,B}(i) = \sum_{j=1}^{i} \frac{k_{F,j}}{k_{A,j+1}} \prod_{k=j}^{i} \frac{k_{A,k+1}}{k_{A,k+1} + k_{F,k} + k_{U,k}} \quad \text{(Equation 34)}$$

The typical range of translation rates in eukaryotic cells is 3.2-5.6 AA per second. Using this range of kA values it was found that equation 34 predicts very similar in vivo co-translational folding trends as are observed experimentally for FRB and HA1; the results when a $k_A$ of 3.9 AA per second is used are displayed here in FIG. 9.

TABLE 5

| Protein | Total codons encoding protein | Codons encoding co-translational folding domain | Length of observable domain | $k_{F,i}$ (s$^{-1}$) | $k_{U,i}$ (s$^{-1}$) | $k_{A,i}$ (AA per second) |
|---|---|---|---|---|---|---|
| SFVP WT | 1,257 | 1-267 | 255 | 0 for i = 1-296<br>20 for i = 297-1,257 | 4.34 × 10$^{-5}$ | 3.9 |
| SFVP ΔC | 1,145 | 1-155 | 143* | 0 for i = 1-184<br>20 for i = 185-1,145 | 4.34 × 10$^{-5}$ | 3.9 |
| Flag-FRB-GFP | 379 | 11-99 | 99 | 0 for i = 1-128<br>15.93 for i = 129-379 | 0.72 | 3.9 |
| HA1 | 565 | 53-275 | 222 | 0 for i = 1-304<br>0.1378 for i = 305-565 | 7.58 × 10$^{-5}$ | 3.9 |

*The last radiolabelled position in SFVP WT is i = 255; the length of the observable domain for SFVP ΔC is therefore 143 (=255-112).

The FactSeq data exhibit large variances in their signal from one codon position to the next, non-zero probabilities within the first fifty codons where folding cannot take place owing to the steric effect of the ribosome exit tunnel, and probabilities >1.0 that arise from a numerator and denominator that are measured in two different experiments. Owing to these poor experimental statistics it is inappropriate to compare the measurements to the detailed, codon-specific predictions of our model. Instead it is justified—as was done in the original FactSeq publication—to interpret the experimental data in terms of unfolded and folded regions along the transcript. Therefore, the FactSeq data and predictions were broken into three regions. Region I corresponds to the first 50 codons of the transcript, and is used as a baseline where any signal from this region must correspond to unfolded protein. Region II was defined to be from codon position 51 to the last codon stated by Han and co-workers to be in the unfolded state. For FRB and both epitopes of HA1 Region II thus consist of codon positions 51-150 and 51-310, respectively. Region III is defined as the codon positions for which the protein is expected to be folded, which is codon positions 151-379 for FRB and codon positions 310-565 for HA1.

Figure 9A:
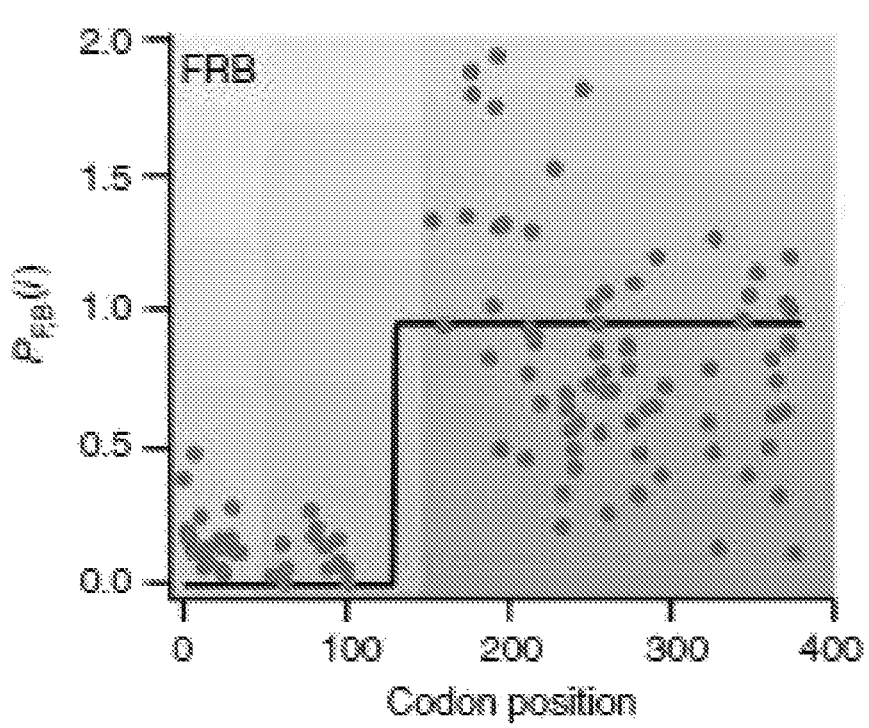
FIG. 9(a-d) shows a comparison between the predicted and experimentally measured FRB and HA1 co-translational folding curves. The co-translational folding probability calculated with equation (34) (bold line) and the experimentally measured-fraction folding using FactSeq (circles) for (a) FRB, HA1 using antibody binding epitope, (b) H28-E23 and (c) Y8-10C2 are shown. The medium values of the FactSeq-measured $P_{F,B,}(i)$ values in (d) are shown with bootstrapped error bars for FRB, H28-E23 and Y8-10C2.
Figure 9B:
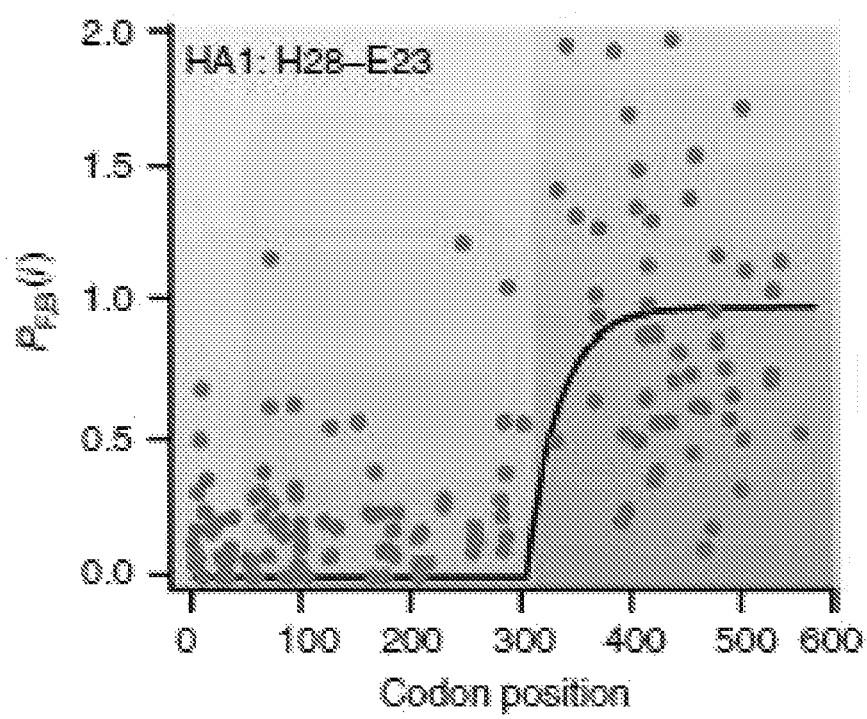
Figure 9C:
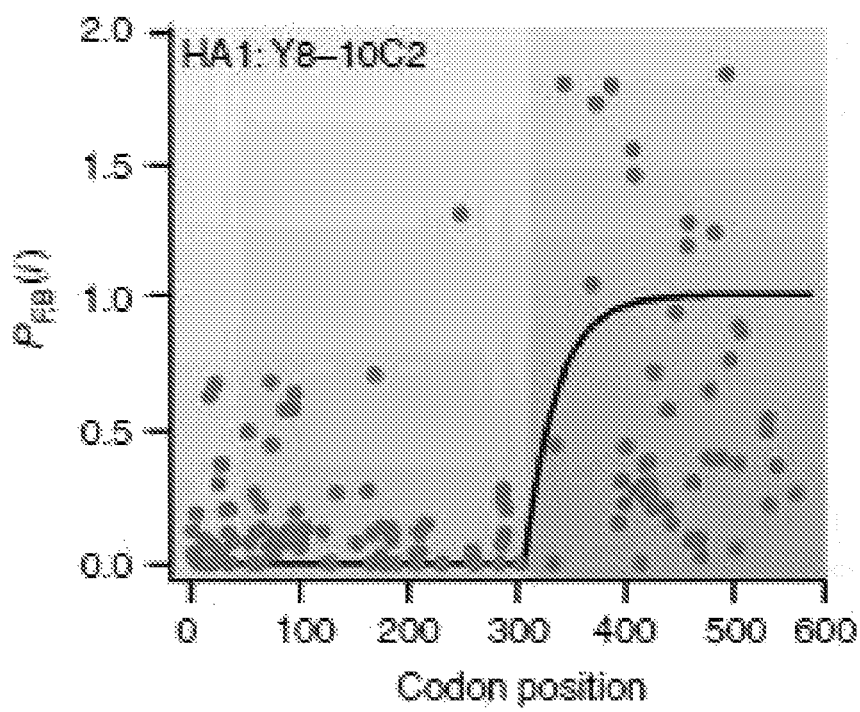
Figure 9D:
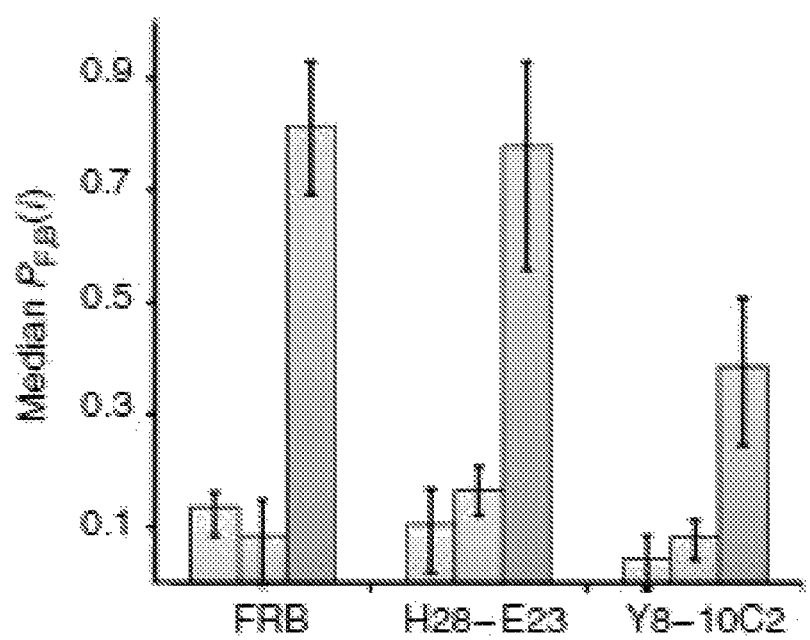

If Region II corresponds to an unfolded protein domain then the median FactSeq signal in this region should be statistically indistinguishable from the median value in Region I. Applicants tested the null hypothesis that the median values in Regions I and II are the same. They applied the Mann—Whitney U-test to this hypothesis and found that Regions I and II are statistically the same (FIG. 9d). The Mann-Whitney U-test was also used to determine that Region III is statistically different from Regions I and II (FIG. 4d). Thus, the experimental data are consistent with the FRB and HA1 folding domains being unfolded in Regions I and II and folded in Region III. These trends in the FactSeq data and our predictions are consistent. These results lend further support to the accuracy of the modelling approach in predicting the experimentally observed co-translational folding profiles.

Example 11

To test the sensitivity of the model's predictions, the Inventors varied the parameters $k_{F,i}$, $k_{U,i}$ and $k_{A,i}$ several fold for each protein. The predicted folding curves for the proteins HA1 and yeast proteins DHOM, DPP3, SBA1, and EF2 (see below) are sensitive to one order of magnitude changes in $k_{F,i}$. On the other hand, the folding curves predicted for DC SFVP, WT SFVP and FRB only visibly shift after a two order of magnitude change in $k_{F,i}$. By varying $k_{U,i}$ by an order of magnitude it was determined that the predicted folding curves for all the proteins are insensitive to this variation in the respective unfolding rates. It was also determined that, for all proteins in this study, except FRB, a twofold change in the global $k_{A,i}$ substantially shifts the co-translational folding curves.

In the case of ΔC SFVP, the Inventors used trial and error to determine the $k_F$ and $k_U$ values needed for Equation 32 to make inaccurate predictions. The $k_F$ and $k_U$ values must change by factors of $10^3$ and $10^6$, respectively, for the predictions to fall outside the error bars. The Inventors also tested how the number of residues that could fit in the ribosome exit tunnel affected the results for DC SFVP and found that their predictions are robust to changes to this value.

The efficiency of co-translational folding can be influenced by the variability in translation rates from one codon position to the next along an mRNA molecule. The previous predictions (FIG. 8) were based on a uniform translation rate (assumption A4) and the sensitivity of the predictions compared to variable rates were tested. Individual codon translation rates in CHO cells, however, have not been measured. There have been at least five different estimates of codon translation rates in other organisms extracted from ribosome profiling data or calculated from theory. These estimated codon translation rates do not correlate with each other, even when calculated for the same organism. Each of the five codon translation rate sets were used to test the sensitivity of the predictions. To apply these rates to CHO cells the Inventors scaled them such that the average codon translation rate across the DC SFVP transcript matched the experimentally measured 3.9 AA per second value.

Using these individual codon translation rates in equation (2), it was found that for four out of the five translation rate sets the predictions are essentially the same as when the average translation rate is used at every codon position. These results indicate that the predictions for DC SFVP are not highly sensitive to variable codon translation rates and that assumption A4 is reasonable for this protein. The Fluitt-Viljoen translation rate estimates are the only ones to result in predicted values that are statistically different from experiment. Therefore, the Inventors hypothesized that either the fastest- or slowest-translating codons in the set of rates predicted by Fluitt and Viljoen were the greatest contributors to the deviations from experiment. To test this hypothesis, the Inventors created two new translation rate data sets. For the first (denoted 'Slow Set') the six slowest-translating sense codons were assigned their Fluitt-Viljoen values and the other 58 codon types were assigned the average rate of 3.9 AA per second. The other set (denoted 'Fast Set') used the six fastest-translating sense codons. Using these new translation-rate estimates in equation (2), the fast set better reproduces the experimental values, while the slow set yields a deviation in the same direction as that observed when the full Fluitt-Viljoen translation rate set is used. This test indicates the greatest contributor to the deviation from experiment is the slowest codon translation rates estimated by Fluitt and Viljoen. It also suggests that, at least for ΔC SFVP synthesis in CHO cells, Fluitt and Viljoen's estimated rates may have too great a variance.

Example 12

Under the same assumptions provided in Example 8, the following equation can be utilized:

$$P_N(j) = \frac{k_{UN}}{k_{UN} + k_{NU}}\left[1 - \left(\frac{\omega^{eff}}{\omega^{eff} + k_{UN} + k_{NU}}\right)^{j-N_d-N_t}\right], \quad \text{(Equation 35)}$$

for $j \geq N_d + N_t$, otherwise $P_N(j)=0$. In equation 1, $k_{UN}$ and $k_{NU}$ are, respectively, the rates of interconversion of the domain from its unfolded to folded state, and from the folded to the unfolded state. $N_d$ is the codon position of the most C-terminal residue in the nascent protein domain of interest and $N_t$ is the number of residues that can fit inside the ribosome exit tunnel. The intrinsic codon translation rate ω has been subsumed in eq. 1 into an effective codon translation rate[18] $\omega^{eff} \equiv \omega x$. For a transcript with ribosome density ρ, $$x = \frac{1 - \rho\ell}{1 + \rho - \rho\ell}$$

is the mean-field probability that there is no ribosome at codon position (j+1)[19] if j is the most 5' codon position occupied by a ribosome. $\omega^{eff}$ accounts for the increase in the time it takes to translate a codon due to the excluded-volume interactions between neighboring ribosomes on a transcript, which provides additional time for folding of the nascent chain.

The main result of l-TASEP (i.e., the expressions for J, FIG. 10b) can be combined with the main result of the master-equation model (i.e., eq. 33) to calculate the rate, F, of synthesis of co-translationally folded protein domains[20] as $$F = JP_N(j=last), \quad \text{(Equation 36)}$$

where $P_N(j=last)$ is the steady-state probability that a particular protein segment (e.g., a domain) will populate its folded state at the stop codon of the transcript. F is equal to the rate of functional nascent protein production for proteins that do not require post-translational modifications. Note also that J and F are functions of $\alpha$, $\beta$, $\omega$, $k_{UN}$, and $k_{NU}$.

Using Equation 36 addresses the first question—does increasing the rate of protein production J always increase the rate of functional nascent protein production F? This question is answered by applying the first-derivative test for monotonicity to F with respect to $\alpha$, $\beta$ and $\omega$. Since the variables that J depends on (i.e., $\alpha$, $\beta$ and $\omega$) change with the translational regime under consideration (FIG. 10b), the derivative of F and J is taken separately in each regime. The derivatives off with respect to $\alpha$, $\beta$ and $\omega$ were always positive meaning that f exhibits monotonic behavior in the L.D. (low density), H.D. (high density) and M.C. (maximal current) regimes—i.e., increases in $\alpha$, $\beta$, or $\omega$ increase or hold constant the rate of protein production per mRNA molecule.

On the other hand, F exhibits non-monotonic behavior in the L.D. and H.D. phases and monotonic behavior in the M.C. phase. Taken together these results mean that there are scenarios within this model (i.e., eq. 36) where increasing protein production rates can decrease the rate at which folded, functional nascent proteins are produced.

To illustrate these scenarios equation 36 is used to calculate the behavior of a hypothetical protein domain that comprises the first 148 N-terminal residues of proteins that are either 228 (in the L.D. and M.C. phases) or 258 (in the H.D.) residues in length. $\alpha$, $\beta$, $\omega$, $k_{UN}$, are varied respectively, between the physiologically-relevant values of 0.001 to 2.000 s$^{-1}$ (refs. Pai, A.; You, L. Mol. Syst. Biol. 2009, 5 (286), 1; Ciandrini, L.; Stansfield, I.; Romano, M. C. PLoS Comput. Biol. 2013, 9 (1)), 0.001 to 5.000 s$^{-1}$, 0.001 to 30.0 s$^{-1}$ (refs. Spencer, P. S.; Siller, E.; Anderson, J. F.; Barral, J. M. J. Mol. Biol. 2012, 422 (3), 328; Nissley, D. A.; Sharma, A. K.; Ahmed, N.; Friedrich, U.; Kramer, G.; Bukau, B.; O'Brien, E. P. Nat. Commun. 2015, Under Review) and 0.001 to 0.5 s$^{-1}$ and then calculate F and J. For each value of $k_{UN}$, $k_{NU}$ was determined by the equation $k_{NU}=k_{UN}e^{-5}$, which is based on the assumption that a typical E. coli protein has a native-state stability of around 5$k_B$T(Ghosh, K.; Dill, K. Biophys. J. 2010, 99 (12), 3996). $N_t$, the number of residues that can fit into the ribosome exit tunnel is 30 residues (O'Brien, E. P.; Christodoulou, J.; Vendruscolo, M.; Dobson, C. M. J. Am. Chem. Soc. 2011, 133 (3), 513). Ribosome profiling experiments (Ingolia, N. T.; Ghaemmaghami, S.; Newman, J. R. S.; Weissman, J. S. 2009, 324 (April), 218) have demonstrated that a ribosome typically covers around 28 to 30 nucleotides from nuclease digestion, therefore l was set to 10 codons.

Figure 11A:
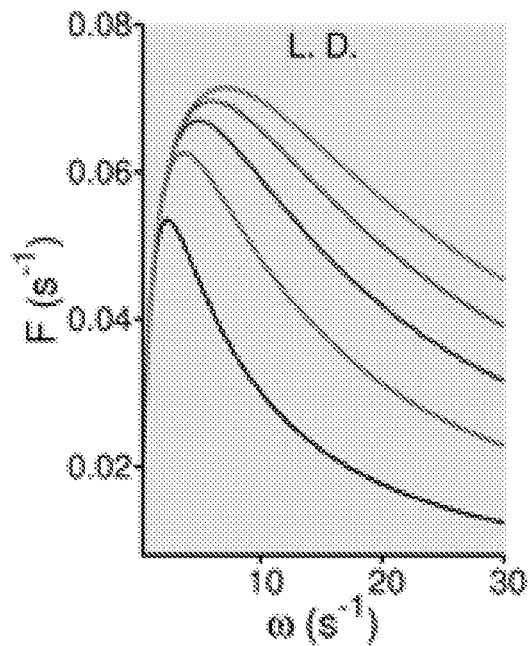
FIG. 11(a-b) shows the behavior of F with respect to $\omega$ in the L.D. phase. Increasing the translation-elongation rate causes non-monotonic behavior in the production of functional nascent protein (a), and non-monotonic behavior in F versus J (b).
Figure 11B:
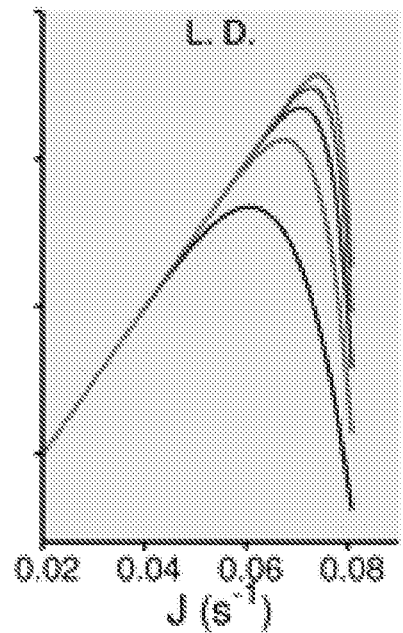

For these hypothetical proteins we find that increasing the translation-elongation rate $\omega$ increases the rate of protein production J in the L.D. regime (data not shown). However, plotting F versus J (FIG. 112B) reveals that at a certain value of $\omega$, increasing the elongation rate further has the effect of increasing J but decreasing F. The reason for this is that at those higher translation-elongation rates, the protein has less time to fold on the ribosome, as illustrated by the decrease in $P_NU$=last). These two opposing effects of speeding up synthesis but decreasing the folding probability give rise to the non-monotonic variation in the production of the functional protein F, as illustrated by the turnover in FIG. 11.

Figure 10A:
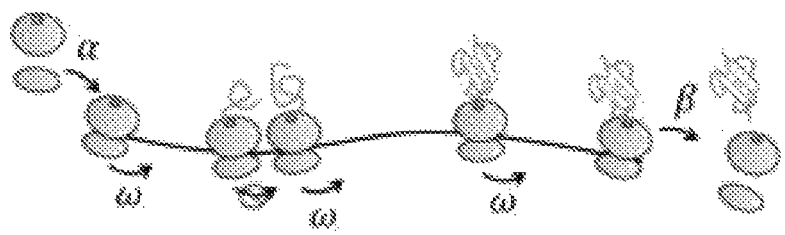
FIG. 10(a) shows an illustration of ribosome traffic on an mRNA molecule and the intrinsic rate variables used in the l-TASEP model.
Figure 10B:
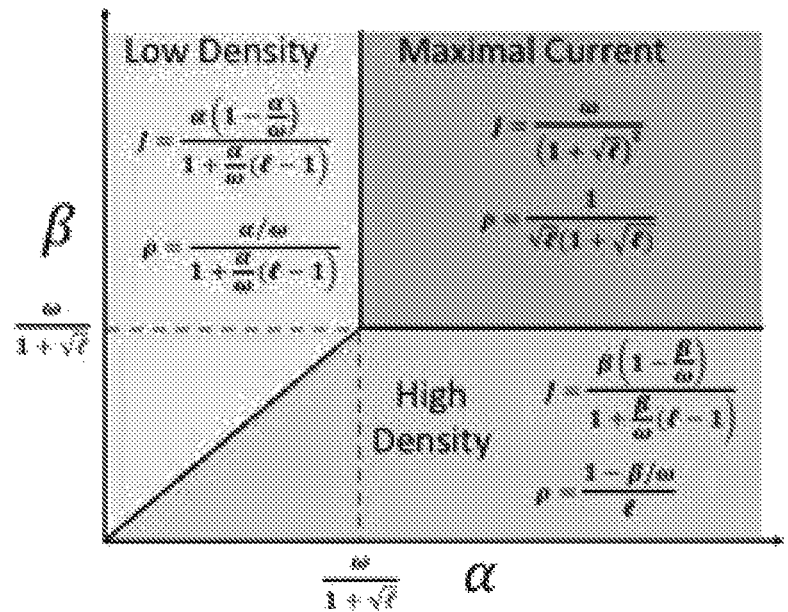
FIG. 10(b) shows the regimes within the l-TASEP model as a function of translation-initiation, $\alpha$, and termination rate $\beta$.

Increasing a in the L.D. regime, however, results in a monotonic increase of both J and F. The reason F does not exhibit a turnover in this case is that an increase in a increases the ribosome density on the transcripts (FIG. 10b). Increased ribosome density on the transcript results in a decreased $\omega^{eff}$, providing more time for domain folding at each codon position. Therefore, both J and $P_N(j=last)$ increase in Equation 36. In the M.C. phase, J is independent of the rate $\alpha$ (FIG. 10b). Therefore, any further increase in $\alpha$ does not increase F.

In the H.D. phase, the rate at which functional protein is produced depends only upon $\beta$ and $\omega$. Here, in contrast to the L.D. phase, increasing $\omega$ results in a monotonic increase in F. The reason for this is that in the H.D. phase, the upper bound of $$\omega^{eff} = \frac{\beta \ell}{1 + \frac{\beta}{\omega}(\ell - 1)}$$

is $\beta$l. In other words, due to the steric hindrance between ribosomes, increasing the intrinsic codon translation rate $\omega$ cannot increase the effective codon translation rate beyond $\omega^{eff}=\beta$l. Therefore, the probability of a domain being in the folded state at the time of nascent chain release cannot decrease beyond a certain threshold probability that depends on the $k_{UN}$ and $k_{NU}$ values.

Figure 12A:
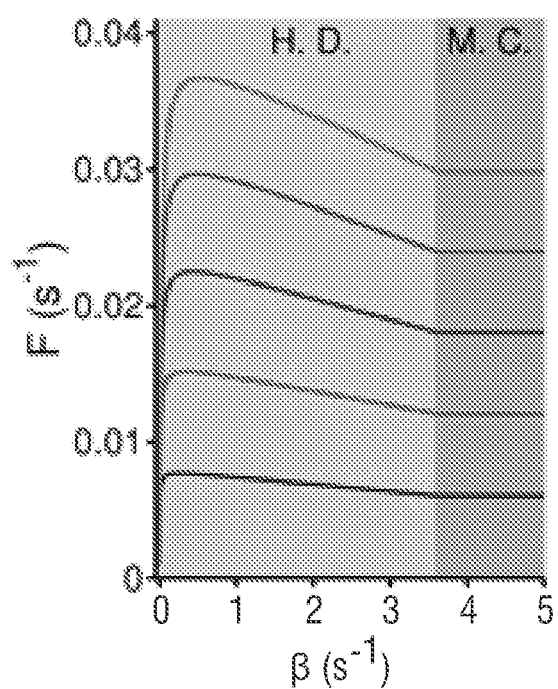
FIG. 12(a-b) shows the behavior of F with respect to $\beta$ in the H.D. phase. Increasing the termination rate, $\beta$, causes non-monotonic behavior in the rate of production of functional nascent protein (a), and non-monotonic behavior in F versus J (b).

In the H.D. regime, increasing the termination rate $\beta$ gives rise to non-monotonic variation in F (FIG. 12a). The reason for this is that increasing $\beta$ in this regime decreases the density of the ribosomes on the transcript (N.B., $$\rho = \frac{1 - \beta/\omega}{\ell},$$

FIG. 10b), thereby increasing the effective codon translation rate $\omega^{eff}$. Increasing $\omega^{eff}$ decreases the probability $P_NU$=last) of successful domain folding by the end of termination because the ribosome spends less time at each codon position. However, increases in $\beta$ increase J (FIG. 10b) These two competing effects are responsible for the non-monotonic variation of F with $\beta$. Note that in FIG. 12a, increasing $\beta$ beyond the value of $$\frac{\omega}{1 + \sqrt{\ell}}$$

shifts the ribosome traffic from the H.D. regime to the M.C. regime where the translation-kinetics is independent of $\beta$ (FIG. 10b).

Figure 12B:
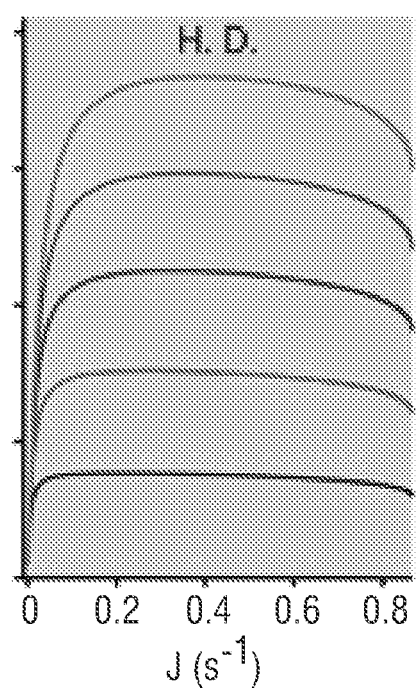

In the M.C. phase, J depends only upon the translation-elongation rate ω. The Inventors found that increasing ω increases F monotonically, but further increases in ω result in a transition into the L.D. regime, where, as described before, increasing ω can decrease F. It is worth mentioning that the larger $\alpha=0.7$ s$^{-1}$ in the following equation $$\frac{dF}{d\omega} = \frac{k_{Un}}{k^{eq}(1+\sqrt{\ell})^2}\left(1 - t^p\left(1 + \frac{pk^{eq}}{\omega x + k^{eq}}\right)\right) \quad \text{(Equation 37)}$$

as compare to the FIG. 12 where $\alpha=0.083$ s$^{-1}$ shifts the turnover of F in the L.D. regime at larger ω values. It is because that at larger a values translation-system requires a larger ω to be in the L.D. regime (FIG. 10b).

The foregoing provides a description of the disclosed systems and methods. Since many embodiments can be made without departing from the spirit and scope of the invention, the invention resides in the claims.

What is claimed is:

1. A method of providing an optimized polynucleotide for production of a protein in a cell, the method comprising:
   searching a source of synonymous codons for an amino acid sequence of said protein;
   selecting a set of codons encoded within said polynucleotide,
      wherein said set of codons optimizes said protein into a desired conformational state, and
      wherein said selecting is not codon harmonization; and
   wherein said selecting comprises:
   (a) obtaining a protein having a known amino acid sequence;
   (b) obtaining conditions for expression of said protein;
   (c) obtaining the rates of translation for said conditions of expression;
   (d) obtaining the conformational states said protein can populate;
   (e) obtaining the rates of interconversion among the states in (d);
   (f) selecting a desired conformational state from (d) for production of said protein; and
   (g) producing an optimized mRNA sequence for said protein in the selected desired conformational state using an algorithm that accounts for (a)-(f); and
   generating said polynucleotide, wherein said polynucleotide encodes said protein.

2. The method of claim 1, further comprising providing to a cell, a polynucleotide comprising or encoding the optimized mRNA sequence for said protein in the selected desired conformational state.

3. The method of claim 1, wherein said translation rates are rates for the elongation phase of translation.

4. The method of claim 1, wherein said translation rates are rates for the initiation phase of translation.

5. The method of claim 1, wherein said translation rates are rates for both initiation phase and elongation phase of translation.

6. The method of claim 1, wherein the protein is a heterologous protein.

7. The method of claim 1, wherein the algorithm includes one or more of Equations 1-39;

$$\frac{dP_l(j,t)}{dt} = \begin{array}{l} \sum_{i=1,i\neq l}^{N} P_i(j,t)k_{il}(j) - \\ \sum_{i=1,i\neq l}^{N} P_l(j,t)k_{li}(j) + P_l(j-1,t)\omega_l(j) - \\ P_l(j,t)\omega_l(j+1) \end{array} \quad \text{(Equation 1)}$$

$$E(\text{new}) = \sum_{j=1}^{N_c} |P_U^{tar}(j) - P_U^{new}(j)| + |P_I^{tar}(j) - P_I^{new}(j)| + |P_F^{tar}(j) - P_F^{new}(j)| \quad \text{(Equation 2)}$$

$$E_\Delta = E(\text{new}) - E(\text{old}) \quad \text{(Equation 3)}$$

$$e^{-E_\Delta/T} \quad \text{(Equation 4)}$$

$$\frac{dP(j,t)}{dt} = M(j)P(j,t) - T(j)P(j-1,t) \quad \text{(Equation 5)}$$

$$P(j,t) = \begin{bmatrix} P_1(j,t) \\ P_2(j,t) \\ \vdots \\ P_N(j,t) \end{bmatrix} \quad \text{(Equation 6)}$$

$$Mj = \quad \text{(Equation 7)}$$

$$\begin{bmatrix} -(\omega_1(j+1) + \sum_{l=1}^{N}k_{1l}) & k_{12}(j) & \cdots & k_{N1}(j) \\ k_{12}(j) & -(\omega_2(j+1) + \sum_{\substack{l=1,\\l\neq 2}}^{N}k_{2l}) & \cdots & k_{N2}(j) \\ \vdots & \cdots & \ddots & \vdots \\ k_{N1}(j) & \cdots & \cdots & -(\omega_N(j+1) + \sum_{l=1}^{N-1}k_{2l}) \end{bmatrix}$$

$$T(j) = \begin{bmatrix} -\omega_1(j) & 0 & \cdots & 0 \\ 0 & -\omega_2(j) & \cdots & 0 \\ \vdots & \vdots & \ddots & \vdots \\ 0 & 0 & \cdots & -\omega_N(j) \end{bmatrix} \quad \text{(Equation 8)}$$

$$P(j) = M(j)^{-1}T(j)P(j-1) \quad \text{(Equation 9)}$$

$$P_i(j) = \frac{\sum_{k=1}^{N_{Traj}}\left[\sum_{\ell=1}^{N_{Frames}(k,j)}\delta_{(i,j,\ell,k)}\Big/\sum_{\ell=1}^{N_{Frames}(k,j)}1\right]}{\sum_{k=1}^{N_{Traj}}} = \quad \text{(Equation 10)}$$

$$\frac{\sum_{k=1}^{N_{Traj}} P_{i,k}(j)}{\sum_{k=1}^{N_{Traj}} 1}$$

$$E_{tot} = E_{bond} + E_{angle} + E_{dihedral} + E_{elec} + E_{LJ} \quad \text{(Equation 11)}$$

$$E_{bond} = \sum_i K_b(r_i - r_0)^2 \quad \text{(Equation 12)}$$

-continued $$E_{angle} = \sum_i \exp(-\gamma K_\alpha(\theta_i - \theta_\alpha)^2 + \epsilon_\alpha) + \exp(-\gamma K_\beta(\theta_i - \theta_\beta)^2)$$ (Equation 13)

$$E_{dihedral} = \sum_{i,j} K_{\psi,j}(1 + (\cos(j\psi - \delta_{ij})))$$ (Equation 14)

$$E_{elec} = \sum_{i,j} \frac{q_i q_j}{4\pi\epsilon_0 \epsilon_r r_{ij}} \exp\left(-\frac{r_{ij}}{\ell_D}\right)$$ (Equation 15)

$$E_{LJ} = \sum_{i,j} \epsilon_{ij}\left[13\left(\frac{\sigma_{ij}}{r_{ij}}\right)^{12} - 18\left(\frac{\sigma_{ij}}{r_{ij}}\right)^{10} + 4\left(\frac{\sigma_{ij}}{r_{ij}}\right)^6\right]$$ (Equation 16)

$$\sigma_{ij} = \frac{\sigma_i + \sigma_j}{2}$$ (Equation 17)

$$Q_{1-2} = \frac{n_{12}}{n_{12}^c}$$ (Equation 18)

$$Q_{12-3} = \frac{n_{12-3}}{n_{12-3}^c}$$ (Equation 19)

$$f(i) = \exp(-k(i)t)$$ (Equation 20)

$$k(i) = \sum_{l=1, l\neq i}^{N} k_{il}$$ (Equation 21)

$$\frac{n(i \to l)}{\sum_{m=1, m\neq i}^{N} n(i \to m)} = \frac{k_{il}}{\sum_{m=1, m\neq i}^{N} k_{im}}$$ (Equation 22)

$$E(MC^k) = \sum_{j=1}^{N_S} |P_U^{opt}(j) - P_U^{MC,k}(j)| + |P_I^{opt}(j) - P_I^{MC,k}(j)| + |P_F^{opt}(j) - P_F^{MC,k}(j)|$$ (Equation 23)

$$\chi(j)\sqrt{\sum_{k=j}^{N_c}((P_U^{org}(k) - P_U^{mut}(k))^2 + ((P_I^{org}(k) - P_I^{mut}(k))^2 + ((P_F^{org}(k) - P_F^{mut}(k))^2}$$ (Equation 24)

$$\Delta(j) = \sqrt{(N_c - j + 1)(P_U^{org}(j) - P_U^{eq}(j))^2 + ((P_I^{org}(j) - P_I^{eq}(j))^2 + ((P_F^{wt}(i) - P_F^{eq}(i))^2}$$ (Equation 25)

$$P_F'(j) = \frac{k_{UF}(j) + \omega^j(j+1)P_F^{wt}(j-1)}{k_{UF}(j) + k_{FU}(j) + \omega^j(j+1)}$$ (Equation 26)

$$P_F^{mut}(j) - P_F^{wt}(j) = A(P_F^{wt}(j) - P_F^{eq}(j))$$ (Equation 27)

$$C_{j+1,k} = \prod_{i=j+1}^{k} \frac{\omega^{wt}(i+1)}{\omega^{wt}(i+1) + k^{eq}(i)}$$ (Equation 28)

$$\chi(j) = |A|B\Delta(j)$$ (Equation 29)

$$A = \frac{\left(\frac{\omega^{mut}(j+1) - \omega^{wt}(j+1)}{\omega^{wt}(j+1)}\right)}{\left(1 + \frac{\omega^{mut}(j+1)}{k^{eq}(j)}\right)}$$ (Equation 30)

$$B = \sqrt{\frac{1 + \sum_{i=j+1}^{N_c} c_{j+1,i}}{N_c - j + 1}}$$ (Equation 31)

$$P_P(t) = \frac{\overbrace{\sum_{i=1}^{M} P_{F,B}(i) f_{L,B}(i,t)}^{\text{Contribution from ribosome-bound and labelled nascent chains}} + \overbrace{\sum_{t'=0}^{t} P_{F,R}(t,t') f_{L,R}(t,t')}^{\text{Contribution from ribosome-released and labelled nascent chains}}}$$ (Equation 32)

$$P_F(t(s)) = \frac{1}{\sum_{i=1}^{M} N_{L,B}(i, t(s)) + \sum_{n=o}^{s} N_{L,R}(t(s), t'(n))} \left[\sum_{i=1}^{M} N_{L,B}(i, t(s))P_{F,B}(i) + \sum_{n=0}^{s} N_{L,R}(t(s), t'(n)) \left(\left[P_{FB}(M) - \frac{k_F}{k_F + k_U}\right]e^{-[k_F+k_U][t(s)-t'(n)]} + \frac{k_F}{k_F + k_U}\right)\right]$$ (Equation 33)

$$P_{F,B}(i) = \sum_{j=1}^{i} \frac{k_{F,j}}{k_{A,j+1}} \prod_{k=j}^{i} \frac{k_{A,k+1}}{k_{A,k+1} + k_{F,k} + k_{U,k}}$$ (Equation 34)

$$P_N(j) = \frac{k_{UN}}{k_{UN} + k_{NU}}\left[1 - \left(\frac{\omega^{eff}}{\omega^{eff} + k_{UN} + k_{NU}}\right)^{j-N_d-N_t}\right]$$ (Equation 35)

$$F = JP_N(j = \text{last})$$ (Equation 36)

$$\frac{dF}{d\omega} = \frac{k_{UN}}{k^{eq}\left(1 + \sqrt{\ell}\right)^2}\left(1 - t^p\left(1 + \frac{pk^{eq}}{\omega x + k^{eq}}\right)\right)$$ (Equation 37)

$$k_{UF}(j) = \frac{k_{UF}(\text{bulk})}{1 + ae^{-j+l+25+\frac{b}{j^c}}}$$ (Equation 38)

$$k_{FU}(j) = k_{FU}(\text{bulk})\left(\frac{1 + e^{-j+l+30}}{d}\right)$$ (Equation 39)

8. The method of claim 2, further comprising producing a protein having the selected desired conformational state.

\* \* \* \* \*